US009403888B2

(12) United States Patent
Khaled

(10) Patent No.: US 9,403,888 B2
(45) Date of Patent: Aug. 2, 2016

(54) COMPOSITIONS AND METHODS FOR PURIFYING BAX

(71) Applicant: UNIVERSITY OF CENTRAL FLORIDA RESEARCH FOUNDATION, INC., Orlando, FL (US)

(72) Inventor: Annette Khaled, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 14/363,793

(22) PCT Filed: Dec. 7, 2012

(86) PCT No.: PCT/US2012/068590

§ 371 (c)(1),
(2) Date: Jun. 7, 2014

(87) PCT Pub. No.: WO2013/086430

PCT Pub. Date: Jun. 13, 2013

(65) Prior Publication Data

US 2014/0349344 A1 Nov. 27, 2014

Related U.S. Application Data

(60) Provisional application No. 61/569,008, filed on Dec. 9, 2011.

(51) Int. Cl.
*C07K 14/47* (2006.01)

(52) U.S. Cl.
CPC ....... *C07K 14/4747* (2013.01); *C07K 2319/036* (2013.01)

(58) Field of Classification Search
None
See application file for complete search history.

(56) References Cited

U.S. PATENT DOCUMENTS

| | | | |
|---|---|---|---|
| 2002/0052316 | A1 | 5/2002 | Shore et al. |
| 2003/0096367 | A1 | 5/2003 | Korsmeyer |
| 2004/0191843 | A1 | 9/2004 | Wright et al. |
| 2010/0099742 | A1 | 4/2010 | Stassi et al. |
| 2014/0255299 | A1 | 9/2014 | Khaled et al. |

FOREIGN PATENT DOCUMENTS

| | | | |
|---|---|---|---|
| CA | 2846629 | | 8/2012 |
| CA | 2846629 | A1 | 2/2013 |
| EP | 12826483.5 | | 8/2012 |
| EP | 2747773 | A2 | 7/2014 |
| NL | WO 2009/145606 | * | 12/2009 |
| WO | PCT/US2012/052354 | | 8/2012 |
| WO | PCT/US2012/068590 | | 12/2012 |
| WO | WO-2013/029011 | A2 | 2/2013 |
| WO | WO-2013/086430 | A1 | 6/2013 |

OTHER PUBLICATIONS

U.S. Appl. No. 61/527,524, filed Aug. 25, 2011, Khaled (Univ. of Central Florida Research Foundation).
U.S. Appl. No. 14/240,801, filed Aug. 24, 2011, Khaled (Univ. of Central Florida Research Foundation).
U.S. Appl. No. 61/569,008, filed Dec. 9, 2011, Khaled (Univ. of Central Florida Research Foundation).
Antonsson, B., et al. "Bax is present as a high molecular weight oligomer/complex in the mitochondrial membrane of apoptotic cells." J. Biol. Chem., vol. 276, pp. 11615-11623 (2001).
Ausili, A., et al. "The interaction of the bax c-terminal domain with negatively charged lipids modifies the secondary structure and changes its way of insertion into membranes." J. Struct. Biol., vol. 164, pp. 146-152 (2008).
Barash, S., et al. "Human secretory signal peptide description by hidden markov model and generation of a strong artificial signal peptide for secreted protein expression." Biochem. Biophys. Res. Commun., vol. 463, pp. 835-842 (2002).
Basanez, G., et al. "Bax-type apoptotic proteins porate pure lipid bilayers through a mechanism sensitive to intrinsic monolayer curvature." J. Biol. Chem., vol. 277, pp. 49360-49365 (2002).
Boohaker, R.J., et al. "Bax supports the mitochondrial network, promoting bioenergetics in nonapoptotic cells." Am. J. Physiol. Cell Physiol., vol. 300, pp. C1466-C1478 (2011).
Brustovetsky, T., et al. "Bax insertion, oligomerization, and outer membrane permeabilization in brain mitochondria: role of permeability transition and SH-redox regulation." Biochim. Biophys. Acta., vol. 1797, pp. 1795-1806 (2010).
Cartron, P.F. et al. "The first alpha helix of bax plays a necessary role in its ligand-induced activation by the BH3-only proteins bid and puma." Mol. Cell, vol. 16(5), pp. 807-818 (2004).
Cartron, P.F., et al. "Distinct domains control the addressing and the insertion of bax into mitochondria." J. Biol. Chem., vol. 280, pp. 10587-10598 (2005).
Cartron, P.F., et al. "The expression of a new variant of the pro-apoptotic molecule bax, baxpsi, is correlated with an increased survival of glioblastoma multiforme patients." Hum. Mol. Genet., vol. 11, pp. 675-687 (2002).
Cartron, P.F., et al. "The n-terminal end of bax contains a mitochondrial-targeting signal." J. Biol. Chem., vol. 278, pp. 11633-11641 (2003).
Deng, J., et al. "BH3 profiling identifies three distinct classes of apoptotic blocks to predict response to ABT-737 and conventional chemotherapeutic agents." Cancer Cell, vol. 12, pp. 171-185 (2007).
Er, E., et al. "Control of bax homodimerization by its carboxyl terminus." J. Biol. Chem., vol. 282, pp. 24938-24947 (2007).
Eskes, R., et al. "Bax-induced cytochrome c release from mitochondria is independent of the permeability transition pore but highly dependent on mg2+ ions." J. Cell Biol., vol. 143, pp. 217-224 (1998).
Garcia-Saez, A.J., et al. "Membrane-insertion fragments of bcl-xl, bax, and bid." Biochemistry, vol. 43, pp. 10930-10943 (2004).
Garcia-Saez, A.J., et al. "Peptides corresponding to helices 5 and 6 of bax can independently form large lipid pores." FEBS J., vol. 273, pp. 971-981 (2006).
Garcia-Saez, A.J., et al. "Peptides derived from apoptotic bax and bid reproduce the poration activity of the parent full-length proteins." Biophys. J., vol. 88, pp. 3976-3990 (2005).

(Continued)

*Primary Examiner* — Doug Schultz
(74) *Attorney, Agent, or Firm* — Meunier Carlin & Curfman LLC

(57) ABSTRACT

Disclosed are compositions and methods for purifying a Bax protein. This abstract is intended as a scanning tool for purposes of searching in the particular art and is not intended to be limiting of the present invention.

10 Claims, 10 Drawing Sheets

(56) References Cited

OTHER PUBLICATIONS

Garcia-Saez, A.J., et al. "Permeabilization of the outer mitochondrial membrane by bcl-2 proteins." Adv. Exp. Med. Biol., vol. 677, pp. 91-105 (2010).
Gavathiotis, E., et al. "Bax activation is initiated at a novel interaction site." Nature, vol. 455(7216), pp. 1076-1081 (2008).
Geisse, S., et al. "Recombinant protein production by transient gene transfer into mammalian cells." Methods Enzymol., vol. 463, pp. 223-238 (2009).
George, N.M., et al. "Bax contains two functional mitochondrial targeting sequences and translocates to mitochondria in a conformational change- and homo-oligomerization-driven process." J. Biol. Chem., vol. 285, pp. 1384 (2010).
Ghibelli, L., et al. "Multistep and multitask bax activation." Mitochondrion, vol. 10, pp. 604-613 (2010).
Han, S-X, et al. "Secretory transactivating transcription-apoptin fusion protein induces apoptosis in hepatocellular carcinoma hepg2 cells." World Journal of Gastroenterology, vol. 14(23), pp. 3642-3649 (2008).
Horie, C., et al. "Characterization of signal that directs c-tail-anchored proteins to mammalian mitochondrial outer membrane." Mol. Biol. Cell, vol. 13, pp. 1615-1625 (2002).
Kaufmann, T., et al. "Characterization of the signal that directs bcl-x(l), but not bcl-2, to the mitochondrial outer membrane." J. Cell Biol., vol. 160, pp. 53-64 (2003).
Kelekar, A., et al. "Bcl-2-family proteins: the role of the bh3 domain in apoptosis." Trends Cell Biol., vol. 8(8), pp. 324-330 (1998).
Leber, B., et al. "Embedded together: the life and death consequences of interaction of the bcl-2 family with membranes." Apoptosis, vol. 12, pp. 897-911 (2007).
del Martinez-Senac, M., et al. "Conformation of the c-terminal domain of the pro-apoptotic protein bax and mutants and its interaction with membranes." Biochemistry, vol. 40, pp. 9983-9992 (2001).
Nechushtan, A., et al. "Conformation of the bax c-terminus regulates subcellular location and cell death." EMBO J., vol. 18, pp. 2330-2341 (1999).
Oltersdorf, T., et al. "An inhibitor of bcl-2 family proteins induces regression of solid tumours." Nature, vol. 435, pp. 677-681 (2005).
Oltvai, Z.N., et al. "Bcl-2 heterodimerizes in vivo with a conserved homolog, bax, that accelerates programmed cell death." Cell, vol. 74, pp. 609-619 (1993).
Putcha, G.V., et al. "Bax translocation is a critical event in neuronal apoptosis: regulation by neuroprotectants, BCL-2, and caspases." J. Neurosci., vol. 19, pp. 7476-7485 (1999).
Robertson, J.D., et al. "Outer mitochondrial membrane permeabilization: an open-and-shut case?" Cell Death Differ., vol. 10, pp. 485-487 (2003).
Roucou, X., et al. "Bax oligomerization in mitochondrial membranes requires tbid (caspase-8-cleaved bid) and a mitochondrial protein." Biochem. J., vol. 368, pp. 915-921 (2002).
Santra, S., et al. "Aliphatic hyperbranched polyester: a new building block in the construction of multifunctional nanoparticles and nanocomposites." Langmuir, vol. 26, pp. 5364 (2010).
Schinzel, A., et al. "Conformational control of bax localization and apoptotic activity by pro168." J. Cell Biol., vol. 164, pp. 1021-1032 (2004).
Schlesinger, P.H., et al. "The bax pore in liposomes." Biophysics, Cell Death Differ., vol. 13, pp. 1403-1408 (2006).
Suzuki, M., et al. "Structure of bax: coregulation of dimer formation and intracellular localization." cell, vol. 103, pp. 645-654 (2000).
Tait, S.W., et al. "Mitochondria and cell death: outer membrane permeabilization and beyond." Nat. Rev. Mol. Cell. Biol., vol. 11, pp. 621-632 (2010).
Valero, J.G., et al. "Bax-derived membrane-active peptides act as potent and direct inducers of apoptosis in cancer cells." J. Cell Sci., vol. 124, pp. 556-564 (2011).
Westphal, D., et al. "Molecular biology of bax and bak activation and action." Biochim. Biophys. Acta, vol. 1813, pp. 521-531 (2011).
Wolter, K.G., et al. "Movement of bax from the cytosol to mitochondria during apoptosis." J. Cell Biol., vol. 139, pp. 1281-1292 (1997).
Youle, R.J., et al. "The bcl-2 protein family: opposing activities that mediate cell death." Nat. Rev. Mol. Cell. Biol., vol. 9, pp. 47-59 (2008).
Zhang, L., et al. "Role of bax in the apoptotic response to anticancer agents." Science, vol. 290, pp. 989-992 (2000).
Zhou, L., et al. "Dynamics and structure of the bax-bak complex responsible for releasing mitochondrial proteins during apoptosis." J. Cell Sci., vol. 121, pp. 2186-2196 (2008).
Preliminary Amendment filed Feb. 25, 2014 for U.S. Appl. No. 14/240,801, filed Feb. 25, 2014 and published as U.S. 2014/0255299 on Sep. 11, 2014 (Inventor—Khaled // Applicant—University of Central Florida Research Foundation, Inc.) (pp. 1-9).
International Search Report and Written Opinion issued Feb. 1, 2013 for International Patent Application No. PCT/US2012/052354, which was filed on Aug. 24, 2012 and published as WO 2013/029011 on Feb. 28, 2013 (Inventor—Khaled // Applicant—University of Central Florida Research Foundation, Inc.) (pp. 1-17).
International Preliminary Report on Patentability issued Apr. 22, 2014 for International Patent Application No. PCT/US2012/052354, which was filed on Aug. 24, 2012 and published as WO 2013/029011 on Feb. 28, 2013 (Inventor—Khaled // Applicant—University of Central Florida Research Foundation, Inc.) (pp. 1-13).
International Search Report and Written Opinion issued Apr. 23, 2013 for International Patent Application No. PCT/US2012/068590, which was filed on Dec. 7, 2012 and published as WO 2013/086430 on Jun. 13, 2013 (Inventor—Khaled // Applicant—University of Central Florida Research Foundation, Inc.) (pp. 1-13).
International Preliminary Report on Patentability issued Jun. 10, 2014 for International Patent Application No. PCT/US2012/068590, which was filed on Dec. 7, 2012 and published as WO 2013/086430 on Jun. 13, 2013 (Inventor—Khaled // Applicant—University of Central Florida Research Foundation, Inc.) (pp. 1-9).
Preliminary Amendment filed Sep. 22, 2014 for U.S. Appl. No. 14/363,793 filed Jun. 7, 2014 (Inventor—Khaled // Applicant—University of Central Florida Research Foundation, Inc.) (pp. 1-5).

* cited by examiner

| | |
|---|---|
| Hmm Bax: | *gaa tcc* atg tgg tgg cgc ctg tgg tgg ctg ctg ctg ctg ctg ctg ctg ctg tgg ccc atg gtg tgg gcc |
| Bax: | atg |
| Hmm Bax: | gac ggg tcc ggg gag cag ccc aga ggc ggg ggg ccc acc agc tct gag cag atc atg aag aca ggg gcc |
| Bax: | gac ggg tcc ggg gag cag ccc aga ggc ggg ggg ccc acc agc tct gag cag atc atg aag aca ggg gcc |
| Hmm Bax: | ctt ttg ctt cag ggt ttc atc cag gat cga gca ggg cga atg ggg ggg gag gca ccc gag ctg gcc ctg |
| Bax: | ctt ttg ctt cag ggt ttc atc cag gat cga gca ggg cga atg ggg ggg gag gca ccc gag ctg gcc ctg |
| Hmm Bax: | gac ccg gtg cct cag gat gcg tcc acc aag aag ctg agc gag tgt ctc aag cgc atc ggg gac gaa ctg |
| Bax: | gac ccg gtg cct cag gat gcg tcc acc aag aag ctg agc gag tgt ctc aag cgc atc ggg gac gaa ctg |
| Hmm Bax: | gac agt aac atg gag ctg cag agg atg att gcc gcc gtg gac aca gac tcc ccc cga gag gtc ttt ttc |
| Bax: | gac agt aac atg gag ctg cag agg atg att gcc gcc gtg gac aca gac tcc ccc cga gag gtc ttt ttc |
| Hmm Bax: | cga gtg gca gct gac atg ttt tct gac ggc aac ttc aac tgg ggc cgg gtt gtc gcc ctt ttc tac ttt |
| Bax: | cga gtg gca gct gac atg ttt tct gac ggc aac ttc aac tgg ggc cgg gtt gtc gcc ctt ttc tac ttt |
| Hmm Bax: | gcc agc aaa ctg gtg ctc aag gcc ctg tgc acc aag gtg ccg gaa ctg atc aga acc atc atg ggc tgg |
| Bax: | gcc agc aaa ctg gtg ctc aag gcc ctg tgc acc aag gtg ccg gaa ctg atc aga acc atc atg ggc tgg |
| Hmm Bax: | aca ttg gac ttc ctc cgg gag cgg ctg ttg ggc tgg atc caa gac cag ggt ggt tgg gac ggc ctc ctc |
| Bax: | aca ttg gac ttc ctc cgg gag cgg ctg ttg ggc tgg atc caa gac cag ggt ggt tgg gac ggc ctc ctc |
| Hmm Bax: | tcc tac ttt ggg acg ccc acg tgg cag acc gtg acc atc ttt gtg gcg gga gtg ctc acc gcc tca ctc |
| Bax: | tcc tac ttt ggg acg ccc acg tgg cag acc gtg acc atc ttt gtg gcg gga gtg ctc acc gcc tca ctc |
| Hmm Bax: | acc atc tgg aag aag atg ggc *ctc gag* |
| Bax: | acc atc tgg aag aag atg ggc |

FIG. 3A

Culture HEK 293T cells stably expressing
Bax cDNA in 20 mL complete DMEM media

Harvest media every 48 hrs

Concentrate using a 3 kD concentrator
spinning at 4000 rcf for 45 min

Run concentrated supernatant through
Superdex 200 size exclusion column at
flow rate of 0.10 mL/min Collect peak fractions and assay for
protein content, concentration,
integrity and activity

```
┌─────────────────────────────────┐
│  Culture HEK 293T cells transiently │
│  expressing Bax cDNA in 500 mL FreeStyle │
│  293 serum free media           │
└─────────────────────────────────┘
            │
            ▼
┌─────────────────────────────────┐
│   Harvest media after 48 hrs    │
└─────────────────────────────────┘
            │
            ▼
┌─────────────────────────────────┐
│ Concentrate using a ultrafilturation cell │
│ concentrator through a 1 kDA filter │
└─────────────────────────────────┘
            │
            ▼
┌─────────────────────────────────┐
│ Run concentrated supernatant through │
│ Uno Q1 ion exchange column at flow │
│ rate of 0.25 mL/min             │
└─────────────────────────────────┘
            │
            ▼
┌─────────────────────────────────┐
│ Run peak fractions through Superdex │
│ 200 size exclusion column at flow rate │
│ of 0.1 mL/min                   │
└─────────────────────────────────┘
            │
            ▼
┌─────────────────────────────────┐
│ Collect peak fractions and assay for │
│ protein content, concentration,  │
│ integrity, and activity         │
└─────────────────────────────────┘
```

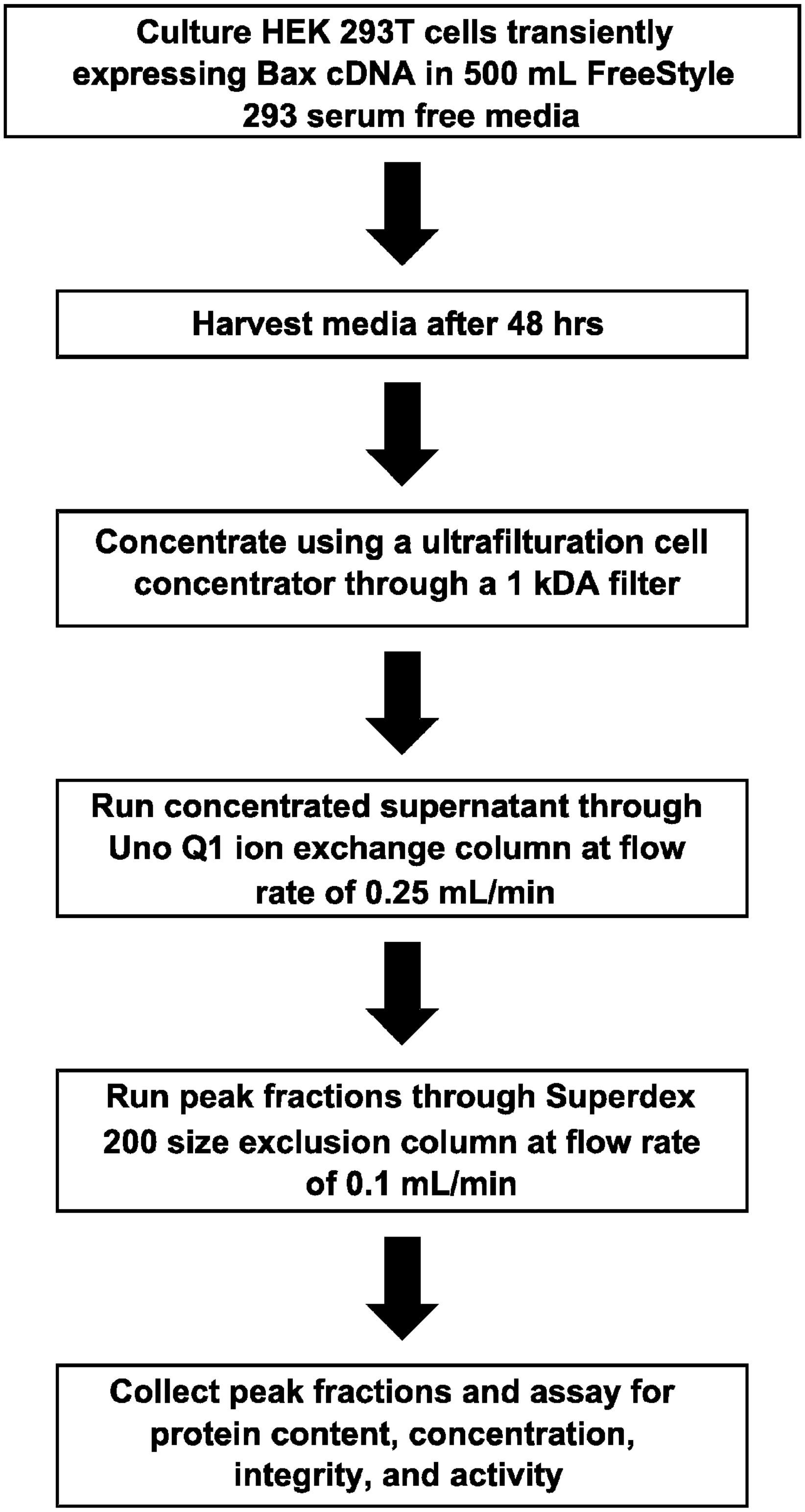

FIG. 4B

COMPOSITIONS AND METHODS FOR PURIFYING BAX

CROSS-REFERENCE TO RELATED APPLICATIONS

This application is a national phase application of PCT/US2012/068590 filed Dec. 7, 2012, which claims priority to U.S. Provisional Patent Application No.61/569,008 filed Dec. 9, 2011, each of which is herein incorporated by reference in its entirety.

STATEMENT REGARDING FEDERALLY SPONSORED RESEARCH

This invention was made with Government support under agency contract/grant number 1RO1GM083324 awarded by the National Institutes of Health. The Government has certain rights in this invention.

BACKGROUND

Cellular homeostasis is regulated by cell renewal and apoptosis. Various apoptotic stimuli result in the recruitment of B cell lymphoma 2 (BCL-2) family proteins to mitochondria, the permeabilization of the outer mitochondrial membrane, the release of cytochrome c, and the activation of caspase, which are followed by processes leading to cell death. Formation of mitochondrial membrane pores is considered a point of no return in terms of cell life or death.

Bax is a 21 kD pro-apoptotic protein of 192 amino acids comprised of 9 alpha helices. Alpha helix 5, which is imbedded within the protein, is the most hydrophobic. Bax also has an extensive hydrophobic groove spanning one face of the protein and is comprised of alpha helices 2, 3, 4, and 5. When Bax is in its cytosolic, monomeric form, the amphipathic alpha 9 helix resides within the groove, and upon conformational change, the helix dissociates from the groove allowing for oligomerization. This conformational change can allow for translocation of Bax to the mitochondrial membrane due to the exposure of the C-terminal helix and relaxation of the bulk of the protein releasing the alpha 5-alpha 6 helices.

Bax was first identified as a protein that associates with and suppresses the anti-apoptotic protein, Bcl-2. As a member of the pro-apoptotic sub-family of Bcl-2 proteins, Bax retains the characteristic helical packing and hydrophobic groove that are the hallmarks of this family. When over-expressed in cells, Bax also causes death. Under non-apoptotic conditions, the localization of Bax is mostly cytosolic, with some mitochondria localization. However, Bax induces apoptosis in response to a variety of death signals, and the association of Bax with mitochondria is linked to the release of cytochrome c, and other death-inducers, from mitochondrial reserves. Data indicate that Bax possesses an intrinsic propensity and capability of membrane pore formation.

Despite advances in understanding the physiology and pathophysiology of cell renewal and apoptosis, there remain many unanswered questions. There is a need for an efficient and inexpensive method of producing and purifying large quantities of Bax protein and Bax protein products. These needs and other needs are satisfied by the present invention.

SUMMARY

Disclosed herein are methods of purifying a Bax protein. Disclosed herein is a method of purifying a Bax protein, comprising modifying a nucleic acid encoding a Bax protein to further encode an HMM peptide, expressing the nucleic acid in a host cell, and purifying the Bax protein. Disclosed herein is a plasmid comprising a nucleic acid encoding a Bax protein, wherein the nucleic acid further encodes an HMM peptide. Disclosed herein is a composition comprising a nucleic acid that encodes a Bax protein. Disclosed herein is a kit comprising a nucleic acid encoding a Bax protein. Disclosed herein is a kit comprising a nucleic acid encoding a Bax protein and instructions for purifying a Bax protein.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1A:
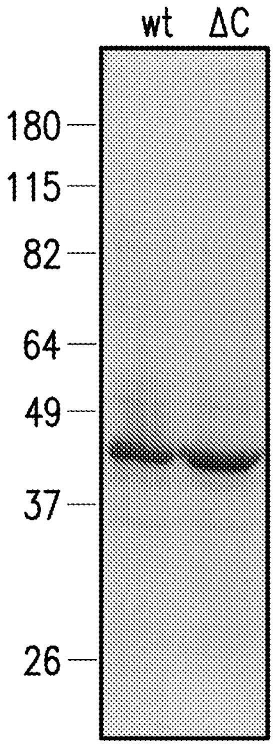
FIG. 1 shows that the conventional expression and purification of proteins is not suitable for expressing and purifying Bax as evidenced by (A) coomassie staining and (B) western blot analysis.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used in the specification and the appended claims, the singular forms “a,” “an” and “the” include plural referents unless the context clearly dictates otherwise.

As used herein, the terms “optional” or “optionally” means that the subsequently described event or circumstance may or may not occur and that the description includes instances where said event or circumstance occurs and instances where it may not.

The word “or” as used herein means any one member of a particular list and also includes any combination of members of that list.

Ranges can be expressed herein as from “about” one particular value, and/or to “about” another particular value. When such a range is expressed, a further aspect includes from the one particular value and/or to the other particular value. Similarly, when values are expressed as approximations, by use of the antecedent “about,” it will be understood that the particular value forms a further aspect. It will be further understood that the endpoints of each of the ranges are significant both in relation to the other endpoint and independently of the other endpoint. It is also understood that there are a number of values disclosed herein, and that each value is also herein disclosed as “about” that particular value in addition to the value itself. For example, if the value “10” is disclosed, then “about 10” is also disclosed. It is also understood that each unit between two particular units is also disclosed. For example, if 10 and 15 are disclosed, then 11, 12, 13, and 14 are also disclosed.

The amino acid abbreviations used herein are conventional letter codes for the amino acids and are expressed as follows: Ala or A for Alanine; Arg or R for Arginine; Asn or N for Asparagine; Asp or D for Aspartic acid (Aspartate); Cys or C for Cysteine; Gln or Q for Glutamine; Glu or E for Glutamic acid (Glutamate); Gly or G for Glycine; His or H for Histidine; Ile or I for Isoleucine; Leu or L for Leucine; Lys or K for Lysine; Met or M for Methionine; Phe or F for Phenylalanine; Pro or P for Proline; Ser or S for Serine; Thr or T for Threonine; Trp or W for Tryptophan; Tyr or Y for Tyrosine; Val or V for Valine.

The phrase “nucleic acid” as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof. For example, in an aspect, a disclosed nucleic acid can encode a Bax protein or Bax protein product, or can encode an HMM peptide or peptide product.

As used herein, the term “determining” can refer to measuring or ascertaining a quantity or an amount or a change in activity. For example, determining the amount of a disclosed polypeptide or a disclosed nucleic acid, such as, for example, a Bax peptide or Bax nucleic acid, in a sample as used herein can refer to the steps that the skilled person would take to measure or ascertain some quantifiable value of the polypeptide or nucleic acid in the sample. The art is familiar with the ways to measure an amount of the disclosed polypeptides and disclosed nucleic acid in a sample.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there is a variety of additional steps that can be performed, it is understood that each of these additional steps can be performed with any specific embodiment or combination of aspects of the methods of the invention.

A weight percent (wt. %) of a component, unless specifically stated to the contrary, is based on the total weight of the formulation or composition in which the component is included.

References in the specification and claims to parts by weight of a particular element or component in a composition denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, the term "level" refers to the amount of a target molecule, such as, for example, a Bax peptide or a Bax nucleic acid, in a sample. The amount of the target molecule such as a nucleic acid or peptide can be determined by any method known in the art and will depend in part on the nature of the molecule (i.e., gene, mRNA, cDNA, protein, enzyme, etc.). The art is familiar with quantification methods for nucleic acids (e.g., genes, cDNA, mRNA, etc.) as well as proteins, polypeptides, enzymes, etc. It is also understood that the amount or level of a target molecule in a sample need not be determined in absolute terms but can be determined in relative terms (e.g., when compared to a control or a sham or an untreated sample).

As used herein, "isolated nucleic acid" or "purified nucleic acid" means DNA that is free of the genes that, in the naturally-occurring genome of the organism from which the DNA of the invention is derived, flank the gene. Therefore, the term includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequences. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

"Polypeptide" as used herein refers to any peptide, oligopeptide, polypeptide, gene product, expression product, or protein, such as, for example, wild-type and mutant Bax peptides and proteins. A polypeptide is comprised of consecutive amino acids. The term "polypeptide" encompasses naturally occurring or synthetic molecules.

As used herein, the term "subject" refers to the target of administration, e.g., an animal. Thus, the subject of the herein disclosed methods can be a vertebrate, such as a mammal, a fish, a bird, a reptile, or an amphibian. In an aspect, the subject is a mammal such as a primate, and, in an aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). The term does not denote a particular age or sex. Thus, adult and newborn subjects, as well as fetuses, whether male or female, are intended to be covered.

As used herein, the term "treatment" refers to the medical management of a patient with the intent to cure, ameliorate, stabilize, or prevent a disease, pathological condition, or disorder. This term includes active treatment directed specifically toward the improvement of a disease, pathological condition, or disorder; causal treatment directed toward removal of the cause of the associated disease, pathological condition, or disorder; palliative treatment designed for the relief of symptoms rather than the curing of the disease, pathological condition, or disorder; preventative treatment directed to minimizing or partially or completely inhibiting the development of the associated disease, pathological condition, or disorder; and supportive treatment directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, intradermal administration, intraperitoneal administration, intrathecal administration, intraocular administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically, that is, administered to treat an existing disease or condition. In further various aspects, a preparation can be administered prophylactically, that is, administered for prevention of a disease or condition.

The term "contacting" as used herein refers to bringing a disclosed compound or a disclosed composition and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$" is intended to refer to the concentration or dose of a substance (e.g., a compound or a drug) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in an in vitro or in vivo system as is convenient and appropriate for the biological response of interest. For example, the response can be measured in vitro using cultured cells or in an ex vivo organ culture system. Alternatively, the response can be measured in vivo using an appropriate research model such as rodent, including mice and rats. The mouse or rat can be an inbred strain with phenotypic characteristics of interest such as cancer or tumors or aberrant cell growth. As appropriate, the response can be measured in a transgenic or knockout mouse or rat wherein a gene or genes have been introduced or knocked-out, as appropriate, to replicate a disease process.

As used herein, "$IC_{50}$" is intended to refer to the concentration or dose of a substance (e.g., a compound or a drug) that is required for 50% inhibition or diminution of a biological process, or component of a process, including a protein, subunit, organelle, ribonucleoprotein, etc. $IC_{50}$ also refers to the concentration or dose of a substance that is required for 50% inhibition or diminution in vivo, as further defined elsewhere herein. Alternatively, $IC_{50}$ also refers to the half maximal (50%) inhibitory concentration (IC) or inhibitory dose of a substance. The response can be measured in an in vitro or in vivo system as is convenient and appropriate for the biological response of interest. For example, the response can be measured in vitro using cultured cells or in an ex vivo organ culture system. Alternatively, the response can be measured in vivo using an appropriate research model such as rodent, including mice and rats. The mouse or rat can be an inbred strain with phenotypic characteristics of interest such as cancer or tumors or aberrant cell growth. As appropriate, the response can be measured in a transgenic or knockout mouse or rat wherein a gene has or genes have been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsulated matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use. Suitable inert carriers can include sugars such as lactose. Desirably, at least 95% by weight of the particles of the active ingredient have an effective particle size in the range of 0.01 to 10 micrometers.

It is understood that the compositions disclosed herein have certain functions. Disclosed herein are certain structural requirements for performing the disclosed functions, and it is understood that there is a variety of structures that can perform the same function that are related to the disclosed structures and that these structures will typically achieve the same result.

1. Bax Proteins

Bax proteins are known in the art, and the skilled person is familiar with the methods for searching, identifying, aligning, and characterizing Bax proteins using available search engines and tools. For example, Accession Nos. Q07812.1 and AAA03619 correspond to the following amino acid sequence for human Bax: MDGSGEQPRG GGPTSSEQIM KTGALLLQGF IQDRAGRMGG EAPELALDPV PQDASTKKLS ECLKRIGDEL DSNMELQRMI AAVDTDSPRE VFFRVAADMF SDGNFNWGRV VALFYFASKL VLKALCTKVP ELIRTIMGWT LDFLRERLLG WIQDQGGWDG LLSYFGTPTW QTVTIFVAGV LTASLTIWKK MG. (SEQ ID NO:1).

In an aspect, a Bax protein can comprise a peptide comprising the C-terminus of full-length Bax. For example, a C-terminus Bax protein can be VTIFVAGVLTASLTIWKKMG, which represents the 20 amino acids at the C-terminus of wild-type Bax (SEQ ID NO:6). In an aspect, a C-terminus Bax peptide can be a variant of wild-type Bax, such as, for example, VTIFVAGVLTASLTIWEEMG (SEQ ID NO:7), VTIFVAGVLTASLTIWLLMG (SEQ ID NO:8), and VTIFVAGVLTASLTIWRRMG (SEQ ID NO:9).

It is understood that as discussed herein the use of the terms homology and identity mean the same thing as similarity. Thus, for example, if the use of the word homology is used between two non-natural sequences, it is understood that this is not necessarily indicating an evolutionary relationship between these two sequences, but rather is looking at the similarity or relatedness between their peptide or nucleic acid sequences. Many of the methods for determining homology between two evolutionarily related molecules are routinely applied to any two or more nucleic acids or two or more peptides or proteins for the purpose of measuring sequence similarity regardless of whether they are evolutionarily related or not. Thus, the Bax nucleic acids and proteins disclosed herein comprise Bax nucleic acids and proteins of multiple species, including but not limited to mouse, human, chicken, pig, rat, cow, chimpanzee, zebra fish, etc. The skilled person is familiar with using various publicly available search engines, such as for example, NCBI databases, to compare two or more nucleic acid or protein sequences.

2. Expression Vectors/Constructs

The term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. The skilled person in the art is familiar with various plasmids and vectors that can be utilized in connection with the disclosed methods and compositions for purifying Bax. Various plasmids and vectors are commercially available.

Suitable expression vectors/constructs for use in the disclosed compositions and disclosed methods for purifying Bax include, but are not limited to, chromosomal, non-chromosomal, and synthetic DNA sequences, e.g., derivatives of SV40, bacterial plasmids, phage DNAs, yeast plasmids, vectors derived from combinations of plasmids and phage DNAs, viral DNA such as vaccinia, adenovirus, fowl pox virus, pseudorabies, baculovirus, and retrovirus. The DNA sequence can be introduced into the expression vector by any suitable procedure.

By "heterologous nucleic acid" is meant that any heterologous or exogenous nucleic acid can be inserted into a vector for transfer into a cell, tissue or organism. The nucleic acid can encode a polypeptide or protein, such as a Bax peptide or an HMM peptide, or an antisense RNA, for example. The nucleic acid can be functionally linked to a promoter. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences.

The terms "transformation" and "transfection" mean the introduction of a nucleic acid, e.g., an expression vector, into a recipient cell, such as a mammalian host cell like HEK and CHO cells, including introduction of a nucleic acid to the chromosomal DNA of said cell.

In the expression systems disclosed herein, preferred promoters controlling transcription from vectors in mammalian host cells can be obtained from various sources including, for example, the genomes of viruses such as polyoma, Simian Virus 40 (SV40), adenovirus, retroviruses, hepatitis B virus and most preferably cytomegalovirus, or from heterologous mammalian promoters, e.g., β-actin promoter. Promoters from the host cell or related species also are useful herein, and can be used for tissue-specific gene expression or tissue-specific regulated gene expression.

In the disclosed expression system, suitable regulatory sequences required for gene transcription, translation, processing and secretion are recognized by those skilled in the art, and are selected to direct expression of the desired protein in an appropriate cell. Accordingly, the term "regulatory sequence" as used herein includes any genetic element present 5' (upstream) or 3' (downstream) of the translated region of a gene, which control or affect expression of the gene, such as enhancer and promoter sequences. Regulatory sequences can be selected by those of ordinary skill in the art for use in connection with the disclosed methods and compositions for purifying Bax.

"Enhancer" generally refers to a sequence of DNA that functions at no fixed distance from the transcription start site and can be either 5' or 3' to the transcription unit. Furthermore, enhancers can be within an intron as well as within the coding sequence itself. Enhancers are usually between 10 and 300 bp in length and function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, fetoprotein and insulin), typically one will use an enhancer from a eukaryotic cell virus for general expression.

In certain embodiments the promoter and/or enhancer region can act as a constitutive promoter and/or enhancer to maximize expression of the region of the transcription unit to be transcribed. In certain constructs the promoter and/or enhancer region are active in all eukaryotic cell types, even if it is only expressed in a particular type of cell at a particular time.

3. Mutations, Substitutions, Insertions, and/or Deletions

The art is familiar with various types of protein and nucleotide modifications including mutations, substitutions, insertions, and/or deletions. Substitutions, deletions, insertions, or any combination thereof may be combined to arrive at a final derivative or analog.

For example, in an aspect, mutant or non-wild-type Bax proteins disclosed herein can comprise one or more insertions. Insertions include amino and/or carboxyl terminal fusions as well as intrasequence insertions of single or multiple amino acid residues. Insertions ordinarily are smaller insertions than those of amino or carboxyl terminal fusions, for example, on the order of one to four residues.

In an aspect, mutant or non-wild-type Bax proteins disclosed herein can comprise one or more substitutional variants, i.e., a polypeptide in which at least one residue has been removed and a different residue inserted in its place. Substitutions generally are made in accordance with the following table and are referred to as conservative substitutions.

| Original Residue | Exemplary Conservative Substitutions |
|---|---|
| Ala | Ser |
| Arg | Gly or Gln |
| Asn | Gln or His |
| Asp | Glu |
| Cys | Ser |
| Gln | Asn or Lys |
| Glu | Asp |
| Gly | Ala |
| His | Asn or Gln |
| Ile | Leu or Val |
| Leu | Ile or Val |
| Lys | Arg or Gln |
| Met | Leu or Ile |
| Phe | Met or Leu or Tyr |
| Ser | Thr |
| Thr | Ser |
| Trp | Tyr |
| Tyr | Trp or Phe |
| Val | Ile or Leu |

Substantial changes in function or immunological identity are made by selecting substitutions that are less conservative than those in the above-provided table, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions that are generally expected to produce the greatest changes in the protein properties are those in which: (a) the hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or hystidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, or (e) by increasing the number of sites for sulfation and/or glycosylation.

Bax proteins and Bax peptides disclosed herein may contain modified amino acids other than the 20 gene-encoded amino acids. The Bax proteins can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation.

B. Plasmids Comprising A Nucleic Acid Encoding A Bax Protein

Disclosed herein is a plasmid comprising a nucleic acid encoding a Bax protein, wherein the nucleic acid further encodes an HMM peptide. In an aspect, a nucleic acid can be cDNA. In an aspect, an HMM peptide can have the amino acid sequence of MWWRLWWLLLLLLLLWPMVWA (SEQ ID NO:2). In an aspect, an HMM peptide can direct Bax to the endoplasmic reticulum. In an aspect, a nucleic acid can encode a wild-type Bax protein. In an aspect, a wild-type Bax protein can be a human Bax protein. For example, in an aspect, a wild-type human Bax protein can be approximately 22 kDa. In an aspect, a Bax protein can be a homologous Bax protein, such as, for example, a wild-type Bax protein from a non-human animal Examples of non-human animals include, but are not limited to, a fish, a bird, a reptile, a frog, a horse, a wild boar, a monkey, a pig, a rabbit, a dog, a sheep, a goat, a cow, a cat, a guinea pig, or a rodent such as, for example, a mouse or a rat. In an aspect, a nucleic acid encoding a wild-type Bax protein and an HMM peptide can comprise the nucleotide sequence of SEQ ID NO:3.

In an aspect, a nucleic acid can encode a mutant or non-wild-type Bax protein. For example, in an aspect, a nucleic acid can encode a Bax protein having one or more mutations, substitutions, insertions, and/or deletions, such as BaxRR. For example, in an aspect, a nucleic acid can encode a Bax protein having a C-terminal and/or an N-terminal deletion. In an aspect, a nucleic acid can encode a Bax protein having one or more mutations, substitutions, and/or deletions in one or more of the 9 alpha-helices of the Bax protein. In an aspect, a nucleic acid can encode a mutant human Bax protein. In an aspect, a nucleic acid can encode a mutant non-human Bax protein. Examples of mutant non-human Bax proteins include, but are not limited to, the Bax protein of a fish, a bird, a reptile, a frog, a horse, a wild boar, a monkey, a pig, a rabbit, a dog, a sheep, a goat, a cow, a cat, a guinea pig, or a rodent such as, for example, a mouse or a rat.

In an aspect, a plasmid comprising a nucleic acid encoding a Bax protein and further encoding an HMM peptide can be stably expressed in a host cell. Host cells can be eukaryotic cells or prokaryotic cells. In an aspect, a disclosed plasmid can be expressed in mammalian host cells such as HEK cells or CHO cells. In an aspect, a disclosed plasmid can be expressed in non-mammalian host cells such as bacterial cells (e.g., *E. coli*) or yeast cells (e.g., *Saccharomyces*). Host cells are well known to the art and can be obtained from commercial sources such as the American Type Culture Collection (ATCC). Host cells can be grown in liquid media culture or on tissue culture plates. The growth conditions can be dependent upon the specific host cells used and such conditions would be known to one of skill in the art. Transfection and growth of host cells are described, for example, in Maniatis et al.

The art is familiar with various host cells and expression systems that produce, in an efficient and inexpensive manner, large quantities of soluble, desirable peptide products, such as, for example, Bax proteins or Bax peptides. For example, in an aspect, an expression system can comprise a pcDNA6 vector. Methods known to one of skill in the art to insert the nucleic acids or polypeptides in host cells are encompassed within this invention. The following are non-limiting examples of such methods: naked DNA transfection, lipofectin-mediated transfer, transformation, micro-injection of nucleic acid into a cell, or calcium-phosphate precipitation transfection methods.

In an aspect of any of the plasmids disclosed herein, an HMM peptide can have an amino acid sequence that has some percent identity to MWWRLWWLLLLLLLLWPMVWA (SEQ ID NO:2). For example, in aspect, an HMM peptide can have an amino acid sequence having 99% percent identity to the sequence set forth in SEQ ID NO:2. In an aspect, an HMM peptide can have an amino acid sequence having 95%-99% percent identity to the sequence set forth in SEQ ID NO:2. In an aspect, an HMM peptide can have an amino acid sequence having 90%-95% percent identity to the sequence set forth in SEQ ID NO:2. In an aspect, an HMM peptide can have an amino acid sequence having 85%-90% percent identity to the sequence set forth in SEQ ID NO:2. In an aspect, an HMM peptide can have an amino acid sequence having 80%-85% percent identity to the sequence set forth in SEQ ID NO:2. In an aspect, an HMM peptide can have an amino acid sequence having 90%-100% percent identity to the sequence set forth in SEQ ID NO:2. In an aspect, an HMM peptide can have an amino acid sequence having 80%-90% percent identity to the sequence set forth in SEQ ID NO:2. In an aspect, an HMM peptide can have an amino acid sequence having 70%-80% percent identity to the sequence set forth in SEQ ID NO:2.

C. Compositions Comprising A Nucleic Acid Encoding A Bax Protein

Disclosed herein is a composition comprising a nucleic acid that encodes a Bax protein. In an aspect, a nucleic acid can be cDNA. In an aspect, a nucleic acid can further encode an HMM peptide. In an aspect, a nucleic acid can encode an HMM peptide having the amino acid sequence of MWWRLWWLLLLLLLLWPMVWA (SEQ ID NO:2). In an aspect, an HMM peptide can direct Bax to the endoplasmic reticulum. In an aspect, a nucleic acid can encode a wild-type Bax protein. In an aspect, a Bax protein can be a human Bax protein. For example, in an aspect, a wild-type human Bax protein can be approximately 22 kDa. In an aspect, a Bax protein can be a homologous Bax protein, such as, for example, a wild-type Bax protein from a non-human animal. Examples of non-human animals include, but are not limited to, a fish, a bird, a reptile, a frog, a horse, a wild boar, a monkey, a pig, a rabbit, a dog, a sheep, a goat, a cow, a cat, a guinea pig, or a rodent such as, for example, a mouse or a rat. In an aspect, a nucleic acid can encode a wild-type Bax protein and an HMM peptide can comprise the nucleotide sequence of SEQ ID NO:3.

Disclosed herein is a composition comprising a nucleic acid that encodes a Bax protein. In an aspect, a nucleic acid can be cDNA. In an aspect, a nucleic acid further can encode an HMM peptide. In an aspect, a nucleic acid can encode a mutant Bax protein. For example, in an aspect, a nucleic acid can encode a Bax protein having one or more mutations, substitutions, insertions, and/or deletions, such as BaxRR. For example, in an aspect, a nucleic acid can encode a Bax protein having a C-terminal and/or an N-terminal deletion. In an aspect, a nucleic acid can encode a Bax protein having one or more mutations, substitutions, and/or deletions in one or more of the 9 alpha-helices of the Bax protein. In an aspect, a nucleic acid can encode a mutant human Bax protein. In an aspect, a nucleic acid can encode a mutant non-human Bax protein. Examples of mutant non-human Bax proteins include, but are not limited to, the mutant Bax protein of a fish, a bird, a reptile, a frog, a horse, a wild boar, a monkey, a pig, a rabbit, a dog, a sheep, a goat, a cow, a cat, a guinea pig, or a rodent such as, for example, a mouse or a rat.

In an aspect, a composition comprising a nucleic acid encoding a Bax protein and further encoding an HMM peptide can be stably expressed in a host cell. Host cells can be eukaryotic cells or prokaryotic cells. In an aspect, a e disclosed nucleic acid can be expressed in mammalian host cells such as HEK cells or CHO cells. In an aspect, a disclosed nucleic acid can be expressed in non-mammalian host cells such as bacterial cells (e.g., E. coli) or yeast cells (e.g., Saccharomyces). Host cells are well known to the art and can be obtained from commercial sources such as the American Type Culture Collection (ATCC). Host cells can be grown in liquid media culture or on tissue culture plates. The growth conditions will be dependent upon the specific host cells used and such conditions would be known to one of skill in the art. Transfection and growth of host cells is described, for example, in Maniatis et al.

The art is familiar with various host cells and expression systems that produce, in an efficient and inexpensive manner, large quantities of soluble, desirable peptide products, such as, for example, Bax. For example, in an aspect, an expression system can comprise a pcDNA6 vector. Methods known to one of skill in the art to insert the nucleic acids or polypeptides in host cells are encompassed within this invention. The following are non-limiting examples of such methods: naked DNA transfection, lipofectin-mediated transfer, transformation, micro-injection of nucleic acid into a cell, or calcium-phosphate precipitation transfection methods.

In an aspect of any of the compositions disclosed herein, the HMM peptide can have an amino acid sequence that has some percent identity to MWWRLWWLLLLLLLLWPMVWA (SEQ ID NO:2). For example, in aspect, an HMM peptide can have an amino acid sequence having 99% percent identity to the sequence set forth in SEQ ID NO:2. In an aspect, an HMM peptide can have an amino acid sequence having 95%-99% percent identity to the sequence set forth in SEQ ID NO:2. In an aspect, an HMM peptide can have an amino acid sequence having 90%-95% percent identity to the sequence set forth in SEQ ID NO:2. In an aspect, an HMM peptide can have an amino acid sequence having 85%-90% percent identity to the sequence set forth in SEQ ID NO:2. In an aspect, an HMM peptide can have an amino acid sequence having 80%-85% percent identity to the sequence set forth in SEQ ID NO:2. In an aspect, an HMM peptide can have an amino acid sequence having 90%-100% percent identity to the sequence set forth in SEQ ID NO:2. In an aspect, an HMM peptide can have an amino acid sequence having 80%-90% percent identity to the sequence set forth in SEQ ID NO:2. In an aspect, an HMM peptide can have an amino acid sequence having 70%-80% percent identity to the sequence set forth in SEQ ID NO:2.

D. Methods Of Using The Compositions And Plasmids

Disclosed herein is a method of purifying a Bax protein, comprising modifying a nucleic acid encoding a Bax protein to further encode an HMM peptide, expressing the nucleic acid in a host cell, and purifying the Bax protein. In an aspect, a nucleic acid can be cDNA. In an aspect, a method can further comprise culturing the host cells in medium. In an aspect, a method can further comprise harvesting the medium. In an aspect, a method can further comprise concentrating the harvested medium. In an aspect, a method can further comprise subjecting the concentrated medium to a size exclusion column and collecting at least one elution fraction. In an aspect, a method can further comprise subjecting at least one elution fraction to liquid chromatography. In an aspect, a method can further comprise assessing Bax protein content, Bax protein concentration, Bax protein conformation integrity, and/or Bax protein activity.

Disclosed herein is a method of purifying a Bax protein, comprising, modifying a nucleic acid encoding a Bax protein to further encode an HMM peptide, expressing the modified nucleic acid in a host cell, culturing the host cells in medium, harvesting the medium, concentrating the harvested medium, subjecting the concentrated medium to a size exclusion column and collecting at least one elution fraction, and subjecting at least one elution fraction to liquid chromatography, thereby purifying the Bax protein. In an aspect, the disclosed method further comprises assessing Bax protein content, Bax protein concentration, Bax protein conformation integrity, and/or Bax protein activity.

In an aspect of a disclosed method of purifying a Bax protein, a nucleic acid can be cDNA. In an aspect, a nucleic acid of the disclosed method can encode a wild-type Bax protein. In an aspect, a wild-type Bax protein is approximately 22 kDa, which corresponds to size of the wild-type human Bax protein. In an aspect, a Bax protein can be a homologous Bax protein, such as, for example, a wild-type Bax protein from a non-human animal. Examples of non-human animals includes, but are not limited to, a fish, a bird, a reptile, a frog, a horse, a wild boar, a monkey, a pig, a rabbit, a dog, a sheep, a goat, a cow, a cat, a guinea pig, or a rodent such as, for example, a mouse or a rat. In an aspect, a HMM peptide can have an amino acid sequence of MWWRLWWLLLLLLLLWPMVWA (SEQ ID NO:2). In an aspect, a HMM peptide can direct Bax to the endoplasmic reticulum. In an aspect, a nucleic acid encoding a wild-type Bax protein and an HMM peptide comprises the nucleotide sequence of SEQ ID NO:3.

In an aspect of a method disclosed herein, an HMM peptide can have an amino acid sequence that has some percent identity to MWWRLWWLLLLLLLLWPMVWA (SEQ ID NO:2). For example, in aspect, an HMM peptide can have an amino acid sequence having 99% percent identity to the sequence set forth in SEQ ID NO:2. In an aspect, an HMM peptide can have an amino acid sequence having 95%-99% percent identity to the sequence set forth in SEQ ID NO:2. In an aspect, an HMM peptide can have an amino acid sequence having 90%-95% percent identity to the sequence set forth in SEQ ID NO:2. In an aspect, an HMM peptide can have an amino acid sequence having 85%-90% percent identity to the sequence set forth in SEQ ID NO:2. In an aspect, an HMM peptide can have an amino acid sequence having 80%-85% percent identity to the sequence set forth in SEQ ID NO:2. In an aspect, an HMM peptide can have an amino acid sequence having 90%-100% percent identity to the sequence set forth in SEQ ID NO:2. In an aspect, an HMM peptide can have an amino acid sequence having 80%-90% percent identity to the sequence set forth in SEQ ID NO:2. In an aspect, an HMM peptide can have an amino acid sequence having 70%-80% percent identity to the sequence set forth in SEQ ID NO:2.

In an aspect of a disclosed method of purifying a Bax protein, a nucleic acid of the disclosed method of purifying a Bax protein can encode a mutant Bax protein. For example, in an aspect, a nucleic acid can encode a Bax protein having one or more mutations, substitutions, insertions, and/or deletions, such as BaxRR. For example, in an aspect, a nucleic acid can encode a Bax protein having a C-terminal and/or an N-terminal deletion. In an aspect, a nucleic acid can encode a Bax protein having one or more mutations, substitutions, and/or deletions in one or more of the 9 alpha-helices of the Bax protein. In an aspect, a nucleic acid can encode a mutant human Bax protein. In an aspect, a nucleic acid can encode a mutant non-human Bax protein. Examples of non-human Bax proteins include, but are not limited to, the Bax protein of a fish, a bird, a reptile, a frog, a horse, a wild boar, a monkey, a pig, a rabbit, a dog, a sheep, a goat, a cow, a cat, a guinea pig, or a rodent such as, for example, a mouse or a rat.

In an aspect, culturing the host cells in medium can comprise stably expressing the nucleic acid in a host cell. Generally, stable expression can be achieved by integration of the gene of interest into the target cell's chromosome. Initially the gene of interest has to be introduced into the cell, subsequently into the nucleus, and finally it has to be integrated into chromosomal DNA. Stably transfected cells can be selected and cultured in various ways, which are known to the art. For example, to facilitate the selection of stably transfected cells, a selection marker can be co-expressed on either the same or on a second, co-transfected vector. A variety of systems for selecting transfected cells exists, including but not limited to conferring to the cells a resistance to antibiotics such as blasticidin or neomycin. Culturing transfected cells can be done either in bulk to obtain a mixed population of resistant cells, or via single cell culture, to obtain cell clones from one single integration event.

In an aspect, host cell of the disclosed method can be eukaryotic cells or prokaryotic cells. In an aspect, host cells can be mammalian host cells such as HEK cells or CHO cells. In an aspect, host cells can be non-mammalian host cells such as bacterial cells (e.g., *E. coli*) or yeast cells (e.g., *Saccharomyces*). Host cells are well known to the art and can be obtained from commercial sources such as the American Type Culture Collection (ATCC). Host cells can be grown in liquid medium culture or on tissue culture plates. The growth conditions will be dependent upon the specific host cells used and such conditions would be known to one of skill in the art. For example, the transfection and growth of host cells are described in Maniatis et al. In an aspect, the host cells can be cultured in Dulbecco's Modified Eagle Medium (DMEM). In an aspect, host cells can be cultured in FreeStyle 293 serum-free medium. DMEM and FreeStyle 293 serum-free medium as well as several other types of medium are known to the art and can be readily purchased from commercial sources. In an aspect, the DMEM and the FreeStyle 293 medium can further comprise fetal bovine serum, penicillin, and/or streptomycin.

In an aspect, harvesting the medium can comprise harvesting the medium one or more times. Methods of harvesting medium are known in the art. As used herein, the term "harvesting" refers to any process by which a cell's or the cells' excreted product or products can be collected from a medium. Harvesting includes, but is not limited to, skimming. In an aspect, harvesting can be non-lethal, i.e., the harvesting process does not kill the cells. In an aspect, harvest can be lethal. In an aspect, a medium in the disclosed method can be harvested every 12 hours, 24 hours, 36 hours, 48 hours, 60 hours, 72 hours, 84 hours, and/or 96 hours. In an aspect, a medium can be harvested at regular intervals, such as, for example, every 6 hours, every 12 hours, every 18 hours, every 24 hours, every 30 hours, every 36 hours, every 42 hours, every 48 hours, every 54 hours, every 60 hours, so forth and so on, for the duration of the existence of the cells. In an aspect, a medium can be harvested one time.

In an aspect, concentrating the harvested medium can comprise centrifugation. In an aspect, a harvested medium can be centrifuged, for example, at 4000 relative centrifugal force or rcf for approximately 45 minutes. In an aspect, a harvested medium can be centrifuged, for example, at an rcf of greater than 4000. In an aspect, a harvested medium can be centrifuged, for example, at an rcf of less than 4000. In an aspect, a harvested medium is centrifuged for more than 45 minutes. In an aspect, a harvested medium can be centrifuged for less than 45 minutes. The art is familiar with the methods and equipment utilized during protein concentration and protein filtration.

In an aspect, concentrating a harvested medium can comprise using a stirred ultrafiltration cell concentrator. In an aspect, the concentrator utilizes a 1 kDa filter.

For example, ultrafiltration (UF) is the process of separating extremely small particles and dissolved molecules from fluids. The primary basis for separation is molecular size, although in all filtration applications, the permeability of a filter medium can be affected by the chemical, molecular or electrostatic properties of the sample. Materials ranging in size from 1 K to 1000 K molecular weight (MW) are retained by certain ultrafiltration membranes, while salts and water will pass through. Colloidal and particulate matter can also be retained. Ultrafiltration membranes can be used both to purify material passing through the filter and also to collect material retained by the filter. Materials significantly smaller than the pore size rating pass through the filter and can be depyrogenated, clarified and separated from high molecular weight contaminants. Materials larger than the pore size rating are retained by the filter and can be concentrated or separated from low molecular weight contaminants. Ultrafiltration is typically used to separate proteins from buffer components for buffer exchange, desalting, or concentration. Ultrafilters are also ideal for removal or exchange of sugars, non-aqueous solvents, the separation of free from protein-bound ligands, the removal of materials of low molecular weight, or the rapid change of ionic and/or pH environment. Depending on the protein to be retained, the most frequently used membranes have a nominal molecular weight limit (NMWL) of 3 kDa to 100 kDa.

As discussed above, in an aspect, a disclosed method further can comprise subjecting of the concentrated medium to a size exclusion column and collecting at least one elution fraction. In an aspect, the size exclusion column can be used in conjunction with liquid chromatography (LC), such as fast protein liquid chromatography (FPLC). Fast protein liquid chromatography (FPLC) is a form of liquid chromatography similar to high-performance liquid chromatography that is used to separate or purify proteins and other polymers from complex mixtures. The FPLC system is a complete system for laboratory scale chromatographic separations of proteins and other biomolecules.

Size-exclusion chromatography (SEC), also called gel-filtration or gel-permeation chromatography (GPC), uses porous particles to separate molecules of different sizes. It is generally used to separate biological molecules, and to determine molecular weights and molecular weight distributions of polymers. Molecules that are smaller than the pore size can enter the particles and therefore have a longer path and longer transit time than larger molecules that cannot enter the particles. Molecules larger than the pore size cannot enter the pores and elute together as the first peak in the chromatogram. This condition is called total exclusion. Molecules that can enter the pores will have an average residence time in the particles that depends on the molecules size and shape. Different molecules therefore have different total transit times through the column. This portion of a chromatogram is called the selective permeation region. Molecules that are smaller than the pore size can enter all pores, and have the longest residence time on the column and elute together as the last peak in the chromatogram. This last peak in the chromatogram determines the total permeation limit.

In an aspect, a method of purifying a Bax protein can further comprise assessing the protein content and protein concentration of the Bax protein. Methods used to assess the content and the concentration of a protein, such as a purified Bax protein, are known in the art. These methods include, but are not limited to, assays such as the Lowry, Bradford, BCA, and UV spectroscopic protein assays. Furthermore, western blotting can be used to identify various proteins in a sample and to confirm the molecular weight of each protein.

In an aspect, a method of purifying a Bax protein can further comprise determining the conformational integrity of the Bax protein. In an aspect, the conformational integrity of the purified Bax protein can be determined through Fourier Transformed Infrared Spectrometry (FT/IR). FT-IR is a preferred method of infrared spectroscopy, and allows identification of the structure composition as either α-helical, β-sheet, or random structure. In infrared spectroscopy, IR radiation is passed through a sample. Some of the infrared radiation is absorbed by the sample and some of it is passed through (transmitted). The resulting spectrum represents the molecular absorption and transmission, creating a molecular fingerprint of the sample. Like a fingerprint, no two unique molecular structures produce the same infrared spectrum.

In an aspect, a method of purifying a Bax protein can further comprise determining whether the Bax protein is functional. In an aspect, the functionality of the purified Bax protein can be determined through surface plasmon resonance (SPR). SPR is an optical phenomenon that provides a non-invasive, label-free means of observing binding interactions between an injected analyte and an immobilized biomolecule in real time. The SPR effect is sensitive to binding of analyte because the associated increase in mass causes a proportional increase in refractive index, which is observed as a shift in the resonance angle. A flow injection analysis configuration is commonly employed in which the analyte of interest, solvated in a buffer solution, is transported across the sensing surface, where it interacts with the immobilized biomolecule. When combined with appropriate surface chemistry, microfluidics and software, this technique is unmatched in its range of applications including: affinity analysis, kinetic analysis, concentration assays, active concentration assays, binding stoichiometry, thermodynamic analysis, study of interaction mechanisms, dependence of interaction on environmental conditions, routine screening, ligand-fishing, and epitope mapping. In an aspect, determining whether the Bax protein is functional comprises other non-SPR activity assays.

In an aspect, a nucleic acid can be cDNA. In an aspect, a nucleic acid of the disclosed method can encode a wild-type Bax protein. In an aspect, a wild-type Bax protein is approximately 22 kDa, which corresponds to size of the wild-type human Bax protein. In an aspect, a Bax protein can be a homologous Bax protein, such as, for example, a wild-type Bax protein from a non-human animal. Examples of non-human animals include, but are not limited to, a fish, a bird, a reptile, a frog, a horse, a wild boar, a monkey, a pig, a rabbit, a dog, a sheep, a goat, a cow, a cat, a guinea pig, or a rodent such as, for example, a mouse or a rat. In an aspect, an HMM peptide can have an amino acid sequence of MWWRLWWLLLLLLLLWPMVWA (SEQ ID NO:2). In an aspect, an HMM peptide can direct Bax to the endoplasmic reticulum. In an aspect, a nucleic acid encoding a wild-type Bax protein and an HMM peptide comprises the nucleotide sequence of SEQ ID NO:3.

In an aspect, a nucleic acid of the disclosed method of purifying a Bax protein can encode a mutant Bax protein. For example, in an aspect, a nucleic acid can encode a Bax protein having one or more mutations, substitutions, insertions, and/or deletions, such as BaxRR. For example, in an aspect, a nucleic acid can encode a Bax protein having a C-terminal and/or an N-terminal deletion. In an aspect, a nucleic acid can encode a Bax protein having one or more mutations, substitutions, and/or deletions in one or more of the 9 α-helices of the Bax protein. In an aspect, a nucleic acid can encode a mutant human Bax protein. In an aspect, the nucleic acid can encode a mutant non-human Bax protein. Examples of non-human Bax proteins include, but are not limited to, the Bax protein of a fish, a bird, a reptile, a frog, a horse, a wild boar, a monkey, a pig, a rabbit, a dog, a sheep, a goat, a cow, a cat, a guinea pig, or a rodent such as, for example, a mouse or a rat.

E. Kits

Disclosed herein is a kit comprising a nucleic acid encoding a Bax protein. In an aspect, the nucleic acid can further encode an HMM peptide. In an aspect, the nucleic acid can comprise the nucleotide sequence of SEQ ID NO:3. In an aspect, an HMM peptide can have the amino acid sequence of MWWRLWWLLLLLLLLWPMVWA (SEQ ID NO:2). In an aspect, the HMM peptide can direct Bax to the endoplasmic reticulum. In an aspect, a nucleic acid can encode a wild-type Bax protein. In an aspect, a Bax protein can be a human Bax protein. For example, in an aspect, a wild-type Bax protein can be approximately 22 kDa, which corresponds to the size of the wild-type human Bax protein. In an aspect, a Bax protein can be a homologous Bax protein, such as, for example, a wild-type Bax protein from a non-human animal. Examples of non-human animals include, but are not limited to, a fish, a bird, a reptile, a frog, a horse, a wild boar, a monkey, a pig, a rabbit, a dog, a sheep, a goat, a cow, a cat, a guinea pig, or a rodent such as, for example, a mouse or a rat. In an aspect, a kit can further comprise host cells, such as mammalian host cells. In an aspect, host cells can be non-mammalian cells. In an aspect, a kit can further comprise instructions for purifying a Bax protein.

Disclosed herein is a kit comprising a nucleic acid encoding a Bax protein. In an aspect, the nucleic acid can further encode an HMM peptide. In an aspect, an HMM peptide can have the amino acid sequence of MWWRLWWLLLLLLLLWPMVWA (SEQ ID NO:2). In an aspect, the HMM peptide can direct Bax to the endoplasmic reticulum. In an aspect, a nucleic acid can encode a mutant Bax protein. For example, in an aspect, a nucleic acid can encode a Bax protein having one or more mutations, substitutions, insertions, and/or deletions, such as BaxRR. For example, in an aspect, a nucleic acid can encode a Bax protein having a C-terminal and/or an N-terminal deletion. In an aspect, a nucleic acid can encode a Bax protein having one or more mutations, substitutions, and/or deletions in one or more of the 9 α-helices of the Bax protein. In an aspect, a nucleic acid can encode a mutant human Bax protein. In an aspect, a nucleic acid can encode a mutant non-human Bax protein. Examples of mutant non-human Bax proteins include, but are not limited to, the mutant Bax protein of a fish, a bird, a reptile, a frog, a horse, a wild boar, a monkey, a pig, a rabbit, a dog, a sheep, a goat, a cow, a cat, a guinea pig, or a rodent such as, for example, a mouse or a rat. In an aspect, a kit can further comprise host cells, such as mammalian host cells. In an aspect, host cells are non-mammalian cells. In an aspect, a kit further can comprise instructions for purifying a Bax protein.

Disclosed herein is a kit comprising a nucleic acid encoding a Bax protein and instructions for purifying a Bax protein. In an aspect, a nucleic acid can further encode an HMM peptide. In an aspect, an HMM peptide can have the amino acid sequence of MWWRLWWLLLLLLLLWPMVWA (SEQ ID NO:2). In an aspect, an HMM peptide can direct Bax to the endoplasmic reticulum. In an aspect, a nucleic acid can encode a wild-type Bax protein. In an aspect, a Bax protein can be a human Bax protein. For example, in an aspect, a wild-type human Bax protein can be approximately 22 kDa. In an aspect, a nucleic acid can comprise the nucleotide sequence of SEQ ID NO:3. In an aspect, a Bax protein can be a homologous Bax protein, such as, for example, a wild-type Bax protein from a non-human animal. Examples of non-human animals includes, but are not limited to, a fish, a bird, a reptile, a frog, a horse, a wild boar, a monkey, a pig, a rabbit, a dog, a sheep, a goat, a cow, a cat, a guinea pig, or a rodent such as, for example, a mouse or a rat. In an aspect, a kit can further comprise host cells. In an aspect, e host cells can be mammalian cells. In an aspect, host cells can be non-mammalian cells.

Disclosed herein is a kit comprising a nucleic acid encoding Bax and instructions for purifying a Bax protein. In an aspect, the nucleic acid can encode a mutant Bax protein. In an aspect, a nucleic acid further can encode an HMM peptide. In an aspect, an HMM peptide can have the amino acid sequence of MWWRLWWLLLLLLLLWPMVWA (SEQ ID NO:2). In an aspect, an HMM peptide can direct Bax to the endoplasmic reticulum. For example, in an aspect, a nucleic acid can encode a Bax protein having one or more mutations, substitutions, insertions, and/or deletions, such as BaxRR. For example, in an aspect, a nucleic acid can encode a Bax protein having a C-terminal and/or an N-terminal deletion. In an aspect, a nucleic acid can encode a Bax protein having one or more mutations, substitutions, and/or deletions in one or more of the 9 alpha-helices of the Bax protein. In an aspect, a nucleic acid can encode a mutant human Bax protein. In an aspect, a nucleic acid can encode a mutant non-human Bax protein. Examples of non-human Bax proteins include, but are not limited to, the Bax protein of a fish, a bird, a reptile, a frog, a horse, a wild boar, a monkey, a pig, a rabbit, a dog, a sheep, a goat, a cow, a cat, a guinea pig, or a rodent such as, for example, a mouse or a rat. In an aspect, the kit can further comprise host cells. In an aspect, e host cells can be mammalian cells. In an aspect, host cells can be non-mammalian cells. In an aspect, a kit can further comprise instructions for purifying a Bax protein.

In an aspect of any of the kits disclosed herein, an HMM peptide can have an amino acid sequence that has some percent identity to MWWRLWWLLLLLLLLWPMVWA (SEQ ID NO:2). For example, in aspect, an HMM peptide can have an amino acid sequence having 99% percent identity to the sequence set forth in SEQ ID NO:2. In an aspect, an HMM peptide can have an amino acid sequence having 95%-99% percent identity to the sequence set forth in SEQ ID NO:2. In an aspect, an HMM peptide can have an amino acid sequence having 90%-95% percent identity to the sequence set forth in SEQ ID NO:2. In an aspect, an HMM peptide can have an amino acid sequence having 85%-90% percent identity to the sequence set forth in SEQ ID NO:2. In an aspect, an HMM peptide can have an amino acid sequence having 80%-85% percent identity to the sequence set forth in SEQ ID NO:2. In an aspect, an HMM peptide can have an amino acid sequence having 90%-100% percent identity to the sequence set forth in SEQ ID NO:2. In an aspect, an HMM peptide can have an amino acid sequence having 80%-90% percent identity to the sequence set forth in SEQ ID NO:2. In an aspect, an HMM peptide can have an amino acid sequence having 70%-80% percent identity to the sequence set forth in SEQ ID NO:2.

In an aspect, a nucleic acid encoding Bax disclosed herein, e.g., a wild-type Bax or homolog thereof or a mutant Bax or homolog thereof, can be stably expressed in a host cell. Host cells can be eukaryotic cells or prokaryotic cells. In an aspect, a nucleic acid can be expressed in mammalian host cells such as HEK cells or CHO cells. In an aspect, a disclosed nucleic acid can be expressed in non-mammalian host cells such as bacterial cells (e.g., *E. coli*) or yeast cells (e.g., *Saccharomyces*). Host cells are well known to the art and can be obtained from commercial sources such as the American Type Culture Collection (ATCC). Host cells can be grown in liquid medium culture or on tissue culture plates. The growth conditions will be dependent upon the specific host cells used and such conditions would be known to one of skill in the art. Transfection and growth of host cells are described, for example, in Maniatis et al.

The art is familiar with various host cells and expression systems that produce, in an efficient and inexpensive manner, large quantities of soluble, desirable peptide products, such as, for example, Bax. For example, in an aspect, an expression system can comprise a pcDNA6 vector. Methods known to one of skill in the art to insert the nucleic acids or polypeptides in host cells are encompassed within this invention. The following are non-limiting examples of such methods: naked DNA transfection, lipofectin-mediated transfer, transformation, micro-injection of nucleic acid into a cell, or calcium-phosphate precipitation transfection methods.

It is contemplated that the disclosed kits can be used in connection with the disclosed methods of making, the disclosed methods of using, and/or the disclosed compositions.

F. Non-medical uses

Also provided are the uses of the disclosed plasmids, cDNAs, nucleic acid, and compositions, as pharmacological tools in the development and standardization of in vitro and in vivo test systems for the evaluation of the effects of Bax on apoptosis in laboratory animals, such as, for example, sheep, cats, dogs, rabbits, monkeys, rats and mice, as part of the search for new therapeutic agents.

G. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Certain materials, reagents and kits were obtained from specific vendors as indicated below, and as appropriate the vendor catalog, part or other number specifying the item is indicated.

1. Conventional Expression and Purification of Bax Proteins

Figure 1B:
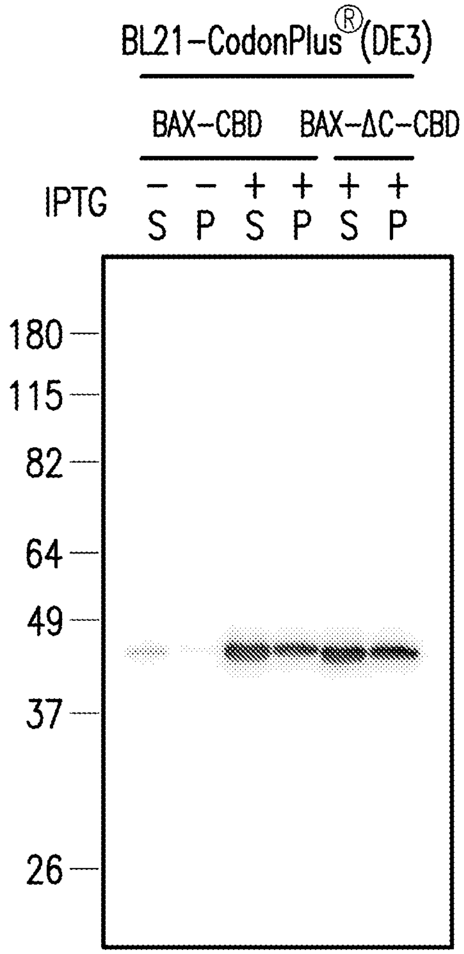

Full-length Bax was cloned into a pTXB1 plasmid. This allowed for the C-terminal linkage of a Chitin Binding Domain (CBD). The Bax-CBD was then inducibly expressed in *E. coli* bacteria by the addition of isopropyl β-D-1-thiogalactopyranoside (IPTG). The bacteria were then harvested and lysed. The Bax-CBD was purified from the lysate by incubating whole cell lysate with chitin beads. FIG. 1A shows a coomassie stained SDS-PAGE gel containing the full length Bax and a C-terminal deleted mutant (ΔC). The estimated size of the uncleaved Bax-CBD was 27 kDa. The coomassie stain showed a single band at ~40 kDa for both the full-length Bax-CBD and AC variant. FIG. 1B shows a western blot analysis. FIG. 1B shows detection of Bax-CBD in both the supernatant (s) and the bacterial pellet (p). This finding indicated that maximum retrieval of the expressed Bax was not easily possible due to the protein being retained in the pellet fraction. Additionally, the western blot confirmed that the Bax protein detected, while containing the correct Bax sequence, was not the correct size for this Bax fusion protein. While dithiothreitol (DTT) could be used as a reducing agent to cleave the CBD from the Bax protein, the use of DTT resulted in cleavage of the Bax protein itself, thereby rendering the Bax protein unusable post cleavage.

2. Generation of an HMM-Bax Plasmid.

As demonstrated in FIGS. 1A and 1B, a conventional bacterial expression system was insufficient to generate viable Bax. This finding was due, in part, to the difficulty of placing a purification tag at the N- or C-terminus of the Bax protein. This is a relevant concern when purifying Bax because both the N- and C-terminals contribute to the stability and inactivity of the monomeric protein.

Figure 2:
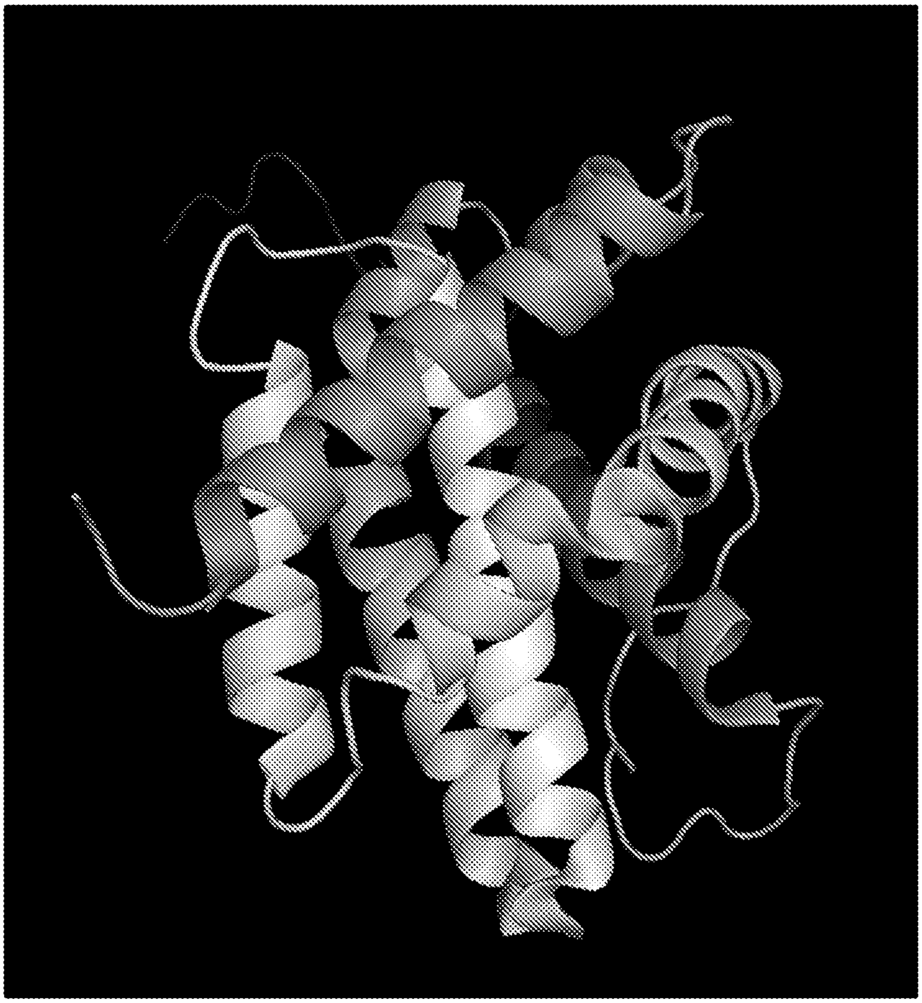
FIG. 2 shows a ribbon structure of wild-type Bax, which comprises nine a helices.

Therefore, an HMM peptide was utilized and served as a secretory signal. The HMM peptide is cleavable by the mammalian protein packaging machinery within the Golgi apparatus. This HMM peptide approach allowed for proper folding and post-translational modification by the endogenous machinery, and allowed for the secretion of Bax out of the cell for a simplified harvesting and purification. FIG. 2 shows the ribbon structure of wild-type Bax without the HMM peptide (see, e.g., NMR study of Bax discussed by Suzuki et al, 2000).

To express Bax in a mammalian expression system, the Bax cDNA was amplified using a forward primer containing an HMM sequence. The HMM nucleotide sequence read as follows: ATG TGG TGG CGC CTG TGG TGG CTG CTG CTG CTG CTG CTG CTG CTG TGG CCC ATG GTG TGG GCC. (SEQ ID NO:4). The HMM-Bax fusion protein was flanked by 5' EcoRI and 3' XhoI restriction sequences to allow for cloning into pcDNA6/His B vector for expression in mammalian system (Invitrogen). Sequencing was done to ensure proper orientation of the cDNA, retention of the mutation, and that the ATG start codon was on the HMM sequence to allow for accurate transcription. FIG. 3A shows the alignment of the HMM-tagged Bax sequence (SEQ ID NO:3) with the non-HMM-tagged Bax sequence (SEQ ID NO:5).

The HMM-tagged Bax cDNA had the following sequence: GAATCC <u>ATGTGGTGGCGCCTGTGGTGGCTGCTGCTGCTGCTGCTGCTGCTGTGGCCCATGGTGTGGGCC</u> GAC GGG TCC GGG GAG CAG CCC AGA GGC GGG GGG CCC ACC AGC TCT GAG CAG ATC ATG AAG ACA GGG GCC CTT TTG CTT CAG GGT TTC ATC CAG GAT CGA GCA GGG CGA ATG GGG GGG GAG GCA CCC GAG CTG GCC CTG GAC CCG GTG CCT CAG GAT GCG TCC ACC AAG AAG CTG AGC GAG TGT CTC AAG CGC ATC GGG GAC GAA CTG GAC AGT AAC ATG GAG CTG CAG AGG ATG ATT GCC GCC GTG GAC ACA GAC TCC CCC CGA GAG GTC TTT TTC CGA GTG GCA GCT GAC ATG TTT TCT GAC GGC AAC TTC AAC TGG GGC CGG GTT GTC GCC CTT TTC TAC TTT GCC AGC AAA CTG GTG CTC AAG GCC CTG TGC ACC AAG GTG CCG GAA CTG ATC AGA ACC ATC ATG GGC TGG ACA TTG GAC TTC CTC CGG GAG CGG CTG TTG GGC TGG ATC CAA GAC CAG GGT GGT TGG GAC GGC CTC CTC TCC TAC TTT GGG ACG CCC ACG TGG CAG ACC GTG ACC ATC TTT GTG GCG GGA GTG CTC ACC GCC TCA CTC ACC ATC TGG AAG AAG ATG GGC CTC GAG. (SEQ ID NO:3) (the HMM tag is underlined).

The non-HMM-tagged Bax cDNA had the following sequence: ATG GAC GGG TCC GGG GAG CAG CCC AGA GGC GGG GGG CCC ACC AGC TCT GAG CAG ATC ATG AAG ACA GGG GCC CTT TTG CTT CAG GGT TTC ATC CAG GAT CGA GCA GGG CGA ATG GGG GGG GAG GCA CCC GAG CTG GCC CTG GAC CCG GTG CCT CAG GAT GCG TCC ACC AAG AAG CTG AGC GAG TGT CTC AAG CGC ATC GGG GAC GAA CTG GAC AGT AAC ATG GAG CTG CAG AGG ATG ATT GCC GCC GTG GAC ACA GAC TCC CCC CGA GAG GTC TTT TTC CGA GTG GCA GCT GAC ATG TTT TCT GAC GGC AAC TTC AAC TGG GGC CGG GTT GTC GCC CTT TTC TAC TTT GCC AGC AAA CTG GTG CTC AAG GCC CTG TGC ACC AAG GTG CCG GAA CTG ATC AGA ACC ATC ATG GGC TGG ACA TTG GAC TTC CTC CGG GAG CGG CTG TTG GGC TGG ATC CAA GAC CAG GGT GGT TGG GAC GGC CTC CTC TCC TAC TTT GGG ACG CCC ACG TGG CAG ACC GTG ACC ATC TTT GTG GCG GGA GTG CTC ACC GCC TCA CTC ACC ATC TGG AAG AAG ATG GGC (SEQ ID NO:5).

Figure 3B:
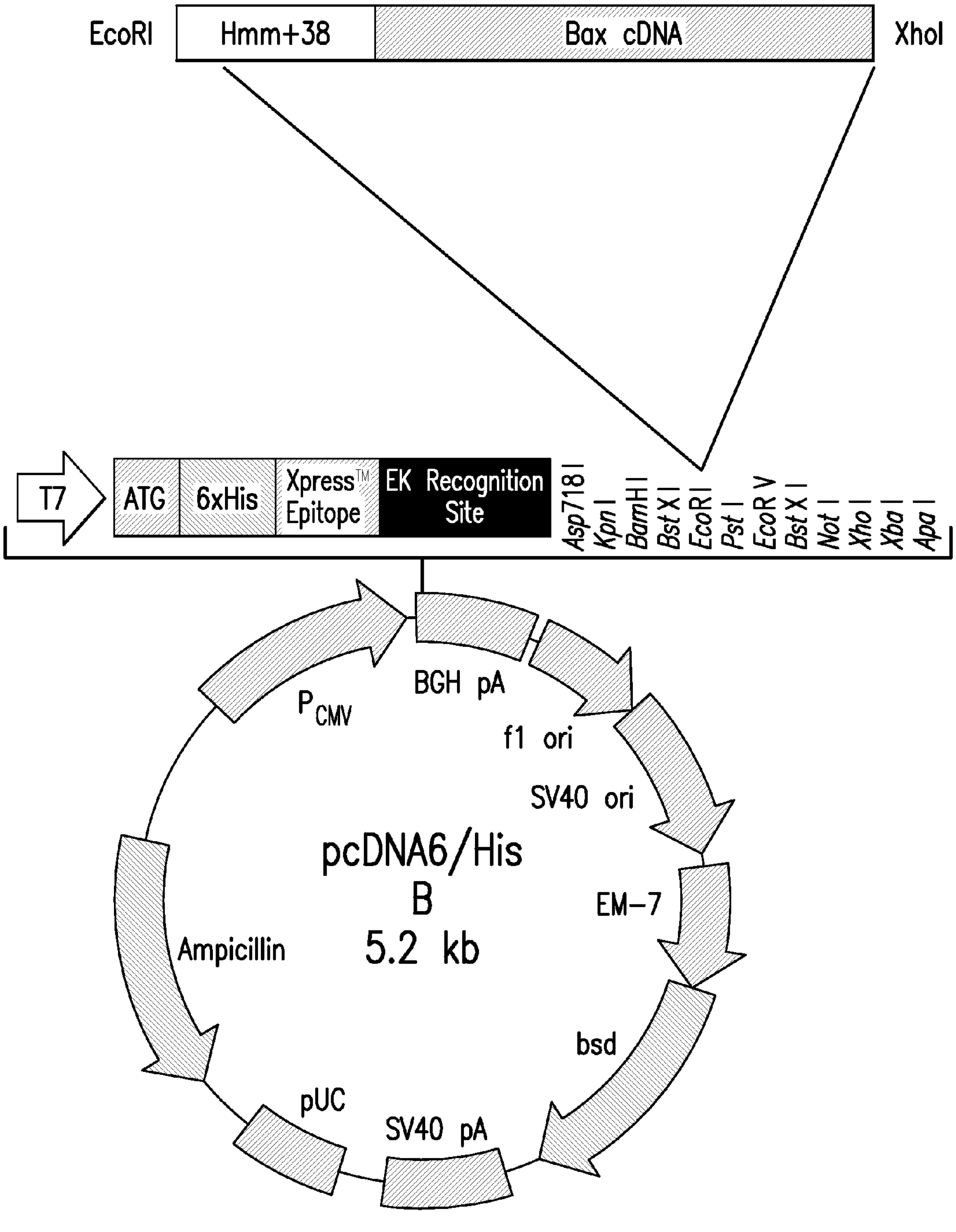
FIG. 3 shows (A) the comparison of the nucleotide sequence for wild-type Bax (SEQ ID NO:5) and wild-type Bax with an HMM peptide, (SEQ ID NO:3), and (B) the structure of a cDNA encoding wild-type Bax and an HMM peptide.

FIG. 3B shows the HMM-tagged Bax cDNA between the EcoRI and XhoI restriction sites and the pcDNA6/HisB vector.

3. Production of Bax.

Figure 4A:
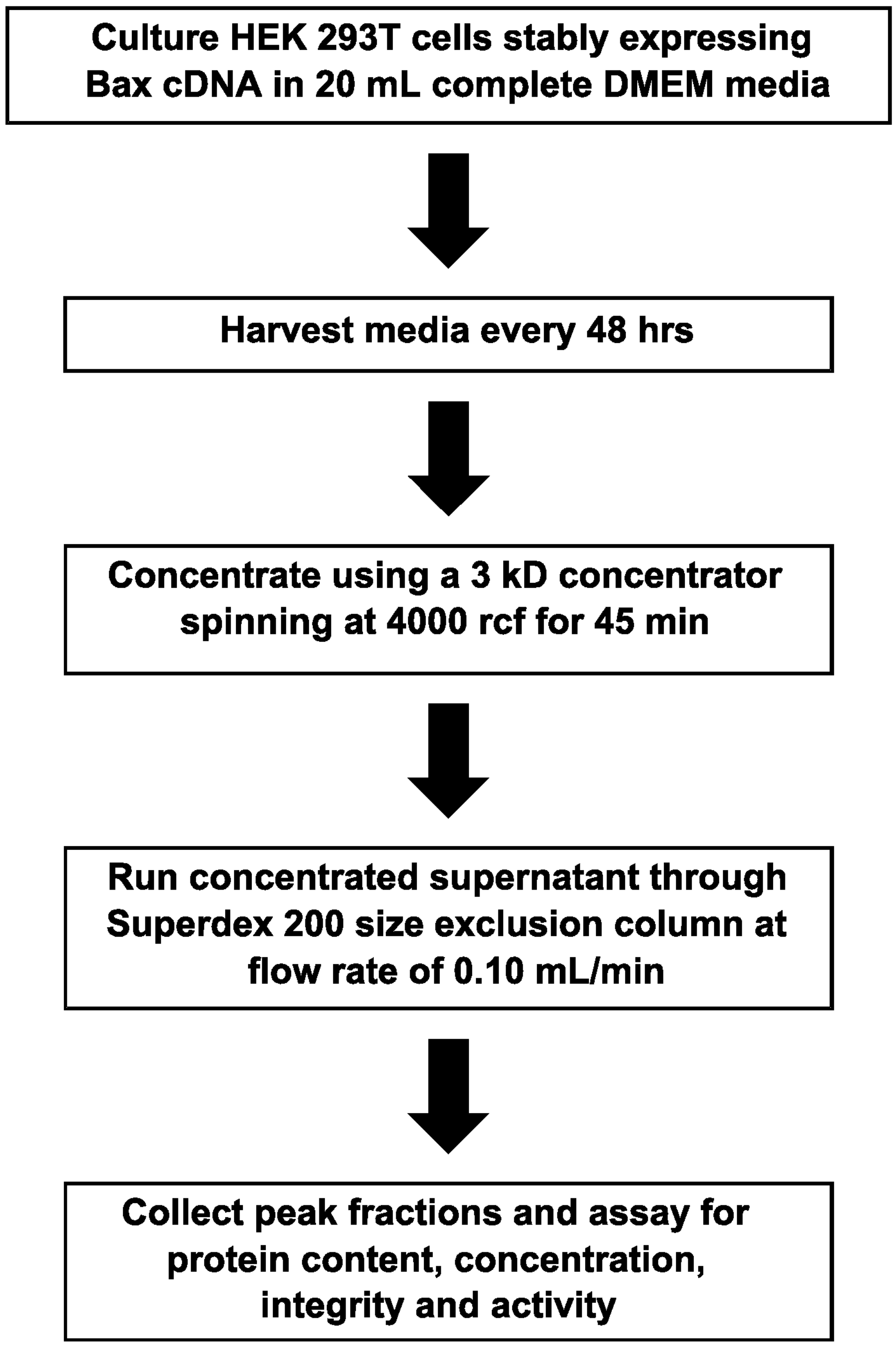
FIG. 4 shows (A) a first schematic for the production, harvesting, and purification of Bax, and (B) a second schematic for the production, harvesting, and the purification of Bax.

FIG. 4A-B show two examples of the protocol used for the production, harvesting, and purification of Bax.

In the first protocol (FIG. 4A), the cDNA for Bax was modified to include the sequence for the HMM secretion signal peptide, MWWRLWWLLLLLLLLWPMVWA (SEQ ID NO:2), and then was cloned into a pcDNA6/HisB mammalian expression vector (See, e.g., FIG. 3B). Sequencing confirmed that the ATG was on the HMM sequence and that the full-length Bax was properly oriented in the vector. The HMM-Bax vector was transfected at a concentration of 1 μg/μL into the Human Embryonic Kidney (HEK) 293T cell line according to the manufacturer's protocol using the Mirus LT-1 transfection kit. Cells were transfected in 6 well plates and then subjected to blasticidin treatment for 2 weeks to select for stably-expressing cells. The cells were grown in Delbucco's Modified Eagles Medium (DMEM, Cellgro) supplemented with 10% FBS (Hyclone) and 1% penicillin/streptomycin. Initial production was scaled up to T75 flasks to maximize protein yield. Fractions were collected and protein concentration was determined by measuring optical density (OD) at 280. The average yield of cytokine were 0.6-0.8 mg/mL. As described in FIGS. 5-7, fractions were subsequently assayed by FT/IR to determine structural integrity, western blot for purity, and were tested in vitro for biological activity.

In the second protocol (FIG. 4B), the cDNA for Bax was modified to include the sequence for the HMM secretion signal peptide, MWWRLWWLLLLLLLLWPMVWA (SEQ ID NO:2), and then was cloned into a pcDNA6/HisB mammalian expression vector. Sequencing confirmed that the ATG was on the HMM sequence and that the full-length Bax was properly oriented in the vector. The HMM-Bax vector was transfected at a concentration of 1 μg/uL into the Human Embryonic Kidney (HEK) 293T cell line using the Polyethylenimene (PEI)-sodium butyrate transfection method. Cells were transfected in hyperflasks (Corning) and were grown in FreeStyle 293 serum free medium (Invitrogen) supplemented with 1% penicillin/streptomycin. The medium were harvested every 48 hours. Fractions were collected and protein concentration determined by measuring optical density (OD) at 280. As described in FIGS. 5-7, fractions were subsequently assayed by FT/IR to determine structural integrity, western blot for purity, and were tested in vitro for biological activity.

4. Harvesting, Concentration, and Purification of Bax.

Figure 5A:
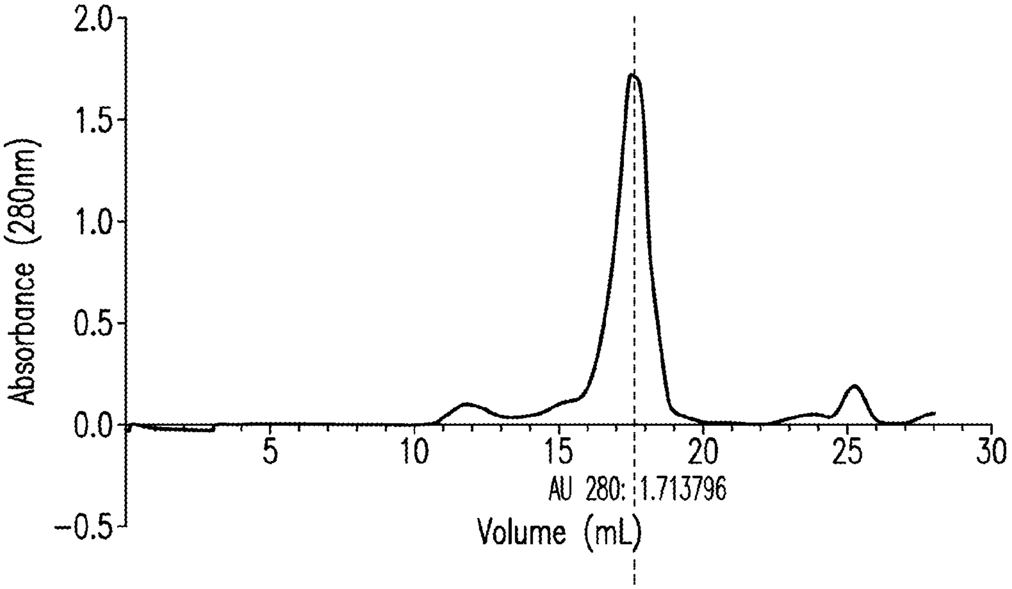
FIG. 5 shows (A) the absorbance of various elutions generated by the size exchange column during the harvesting and purification of Bax when coupled to FPLC, and (B) that the purified Bax had the correct molecular weight.
Figure 5B:
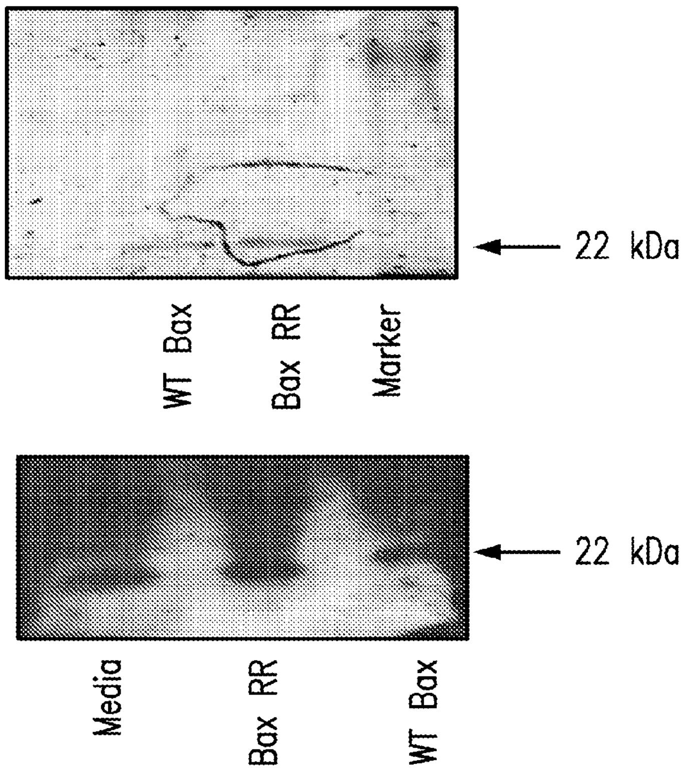

In a first approach to harvesting, concentrating, and purifying Bax, the HMM protein sequence allowed for secretion of the protein into the medium. The medium were collected at 48 hour increments, and each 20 mL collected volume was concentrated down to 2 mL by centrifugation (Eppendorf) at 4000 rpm for 45 min through a 3,000 dalton (da) concentrator (Millipore). The concentrated medium were loaded in 1 mL increments onto a Superdex 200 size exclusion column (GE). (See, e.g., FIG. 4). The column was attached to a BioLogic DuoFlow Fast Protein Liquid Chromatography (FPLC) machine (BioRad) and the sample was run through the column at a flow rate of 10 μL/min to allow for maximum resolution of peak fractions. The running buffer was a Hepes buffer (20 mM Hepes, 120 mM NaCl, 50 mM L-Arginine, 50 mM L-Glutamic Acid). Potassium hydroxide (KOH) was used to achieve a pH of 7.2. Based on the size of Bax (~22 kDa) and the specifications of the Superdex 200 column, the predicted elution volume of a protein of this size was at ~17 mL. Based on a representative chromatograph of the absorbance units (AU) at 280 nm, the peak absorbance occurs at 17.7 mL. The entire $17^{th}$ mL, as well as the flanking volumes were collected to assay for protein concentration by OD 280 and the concentration was determined to be ~0.65 mg/mL. (FIG. 5A). FIG. 5A shows a gel stained for total protein, which indicates that the Bax protein is the correct size. The gel in FIG. 5A was subsequently transferred to a membrane and blotted for Bax using an anti-Bax antibody. Western blotting using N20 (Santa Cruz) as the primary antibody was used to confirm the presence of the wild-type Bax protein (22 kD) as well as a mutant form of Bax (BaxRR) in which E69 and N73 were mutated to arginines.

In a second approach to harvesting, concentrating, and purifying Bax, the HMM protein sequence allowed for secretion of the protein into the medium. Medium were collected at 48 hour increments, and the 550 mL collected volume was concentrated down to 10 mL using low flow $N_2$ gas in a stirred ultrafiltration cell with a 1 kDa filter (Millipore). The concentrated medium was loaded in onto a Uno Q1 ion exchange column (BioRad). The column was attached to a BioLogic DuoFlow Fast Protein Liquid Chromatography (FPLC) machine (BioRad) and the sample was run through the column at a flow rate of 250 μL/min. The running buffer was a Bis-Tris buffer (10 mM Bis-Tris-HCl Buffer, pH 7, 50 mM Arg 50 mM Glu), using potassium hydroxide (KOH) to achieve a pH of 7.0. The elution buffer was running buffer with 1M KCl. The peak fractions were then run through a Superdex 200 size exclusion column (GE Healthcare) at a flow rate of 100 μL min to allow for maximum resolution. Based on the size of Bax (21.239 kDa) and the specifications of the Superdex 200 column, the predicted elution volume of a protein of this size was at ~17 mLs. Based on a representative chromatograph of the absorbance units (AU) at 280 nm, the peak absorbance occurs at 17.7 mLs. The entire $17^{th}$ mL, as well as the flanking volumes were collected to assay for protein concentration by OD 280 and the concentration was determined to be ~0.130 mg/mL. The table below shows the protein concentrations calculated by A280.

| | A | ϵ ($M^{-1} cm^{-1}$) | c (M) | 1 (CM) | mol wt (g/mol) | c (g/l) | μg in 200 μL |
|---|---|---|---|---|---|---|---|
| SEC concentrate | 0.442 | 35980 | 3.07123E−05 | 0.4 | 21184 | 0.651 | 130.122 |
| 1 μL/200 μL | 0.015 | 35980 | 1.07374E−06 | 0.4 | 21184 | 0.023 | 4.549 |
| 3 μL/200 μL | 0.017 | 35980 | 1.19293E−06 | 0.4 | 21184 | 0.025 | 5.054 |
| IEC concentrate | 0.297 | 35980 | 2.06674E−05 | 0.4 | 21184 | 0.438 | 87.564 |
| 3 μL/200 μL | 0.048 | 35980 | 3.36256E−06 | 0.4 | 21184 | 0.071 | 14.247 |
| 6 μL/200 μL | 0.081 | 35980 | 5.60728E−06 | 0.4 | 21184 | 0.119 | 23.757 |

5. Verification of Activity of Purified Bax.

The ability for Bax to bind to itself is integral to its apoptotic activity. Therefore, to assess the biological activity of the purified Bax protein, the binding capability was assessed by surface plasmon resonance (SPR). Monomeric Bax was covalently linked by amine coupling to an activated polyethylene glycol coated gold sensor. The immobilized Bax originated from fraction 17 of the size exclusion chromatography. (See FIG. 5). The immobilized Bax was at a concentration of 40 µg/mL and was in a sodium acetate buffer with a pH of 3.5. Serial dilutions of full-length Bax were then injected over the plate containing the immobilized Bax. The samples were serially diluted from a 2000 nM stock and incubated at 37° C. Injections were done in duplicate and for 420 sec each. The running buffer was a Hepes buffer (20 mM Hepes, 120 mM NaCl, 50 mM L-Arginine, 50 mM L-Glutamic Acid). Potassium hydroxide (KOH) was used to achieve a pH of 7.2. The plate was regenerated after each injection with 2M NaCl for 90 sec. The association (Ka=$1.194^{10}$), dissociation (Kd=0.05612), and total binding constant ($K_D$=46.9918 nM) were then calculated for wild-type Bax (at pH 7.2) using the Scrubber2 program (BioLogic Software). The percent capacity was also determined and the highest concentration injection being bound by >80% of the immobilized Bax. As there was only one slope and no increase, there was no secondary binding (that is, there was only binding to the plate).

Figure 6A:
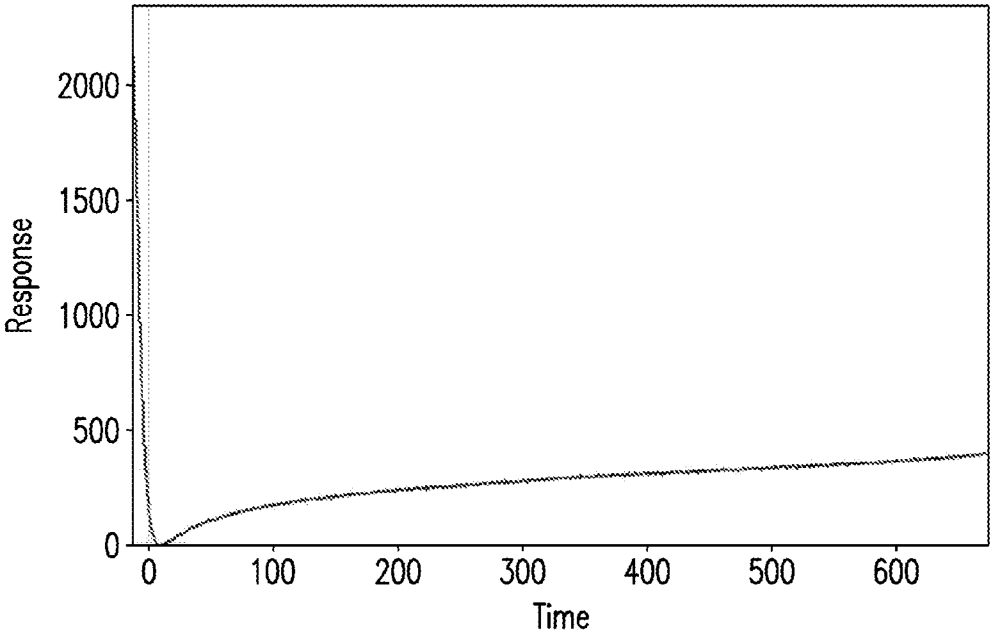
FIG. 6 (A)-(B) shows that secreted Bax retained activity.
Figure 6B:
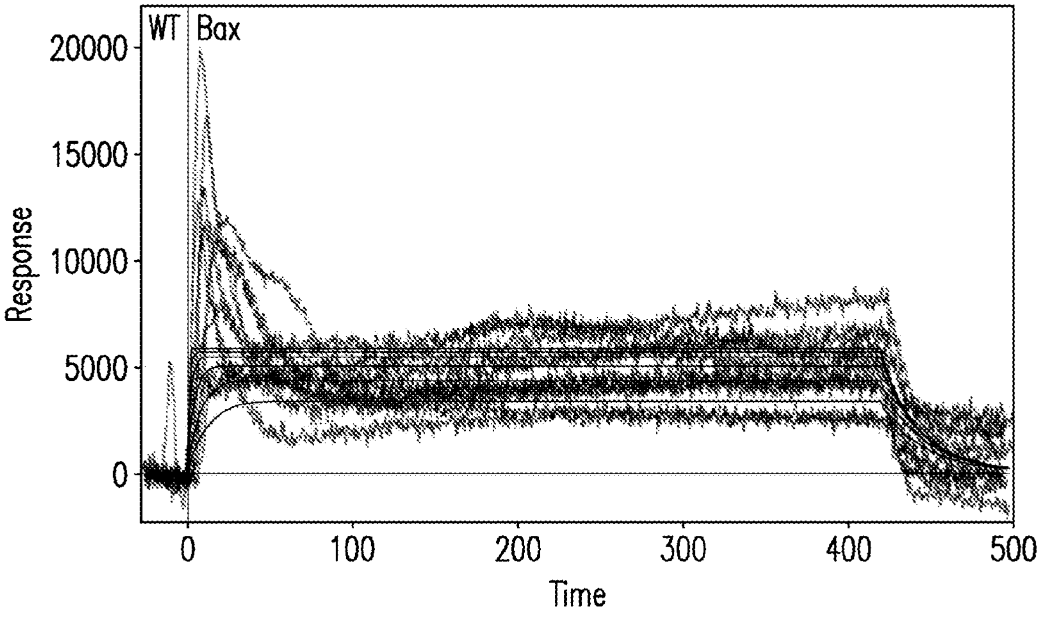

In FIG. 6A, wild-type Bax (WT Bax) was attached to the SPR plate and buffer washed over it. Over time, there was no decrease in the signal, which indicates that a single layer of monomeric Bax had attached to plate. To measure the formation of Bax dimers, serial dilutions of WT Bax were passed over the immobilized Bax on the plate. Association, dissociation and binding constants for Bax dimerization were determined from the data shown in FIG. 6B. These data indicate that WT Bax produced through the claimed method of expression and purification undergoes dimerization.

6. Determination of Secondary Structure of Purified Bax.

Figure 7A:
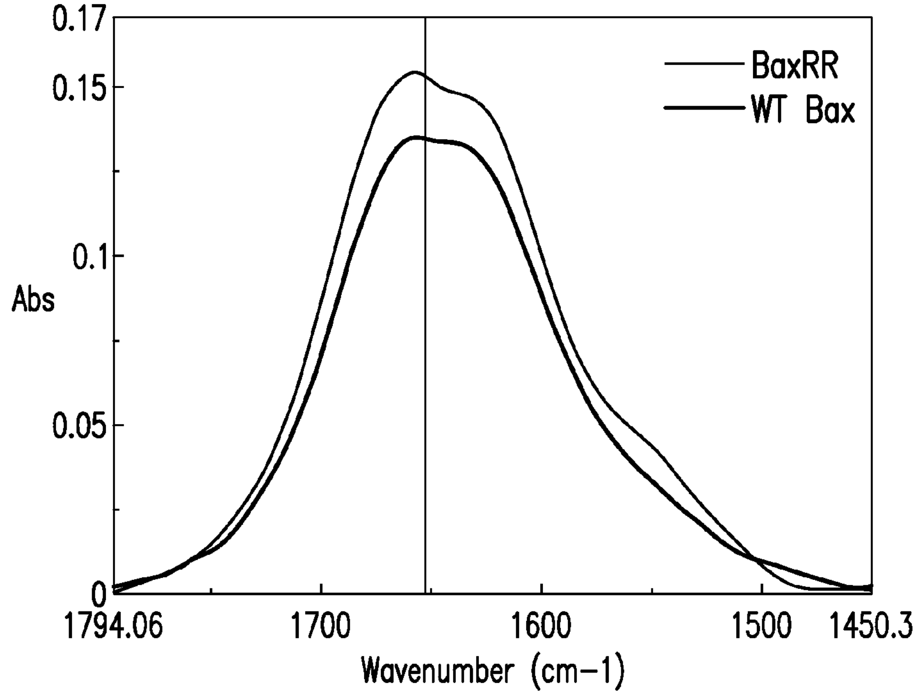
FIG. 7 shows the determination of the secondary structure of secreted Bax via (A) Fourier Transformed Infrared Spectrometry and (B) Circular Dichromism.

The retention of secondary structure throughout the purification process is necessary to assess the true biological function of the purified Bax. Fourier Transformed Infrared Spectrometry (FT/IR) allows identification of the structure composition as either α-helical, β-sheet, or random structure. 30 µL of the sample from fraction 17 of the size exclusion column was placed between two calcium fluoride windows with a 6 µm spacer. This sandwich assembly was then placed in the FT/IR machine (Jasco) and scanned 200 times. Each IR spectrum was normalized to a buffer only loading control and was background subtracted. As shown in FIG. 7, the resulting spectrum of Bax (WTBax) showed a tight α-helical component at 1660 $cm^{-1}$ and a contributing 13 structure at ~1620 $cm^{-1}$ (blue line). A comparison of a Bax mutant (BaxRR) (red line) generated using the same method showed that the Bax mutant has a slightly more relaxed α-helical component that has red shifted (>1660 $cm^{-1}$), as well as an increase in random structure, which is indicated by the shoulder at 1550 $cm^{-1}$. This result was congruent with expectations that the isolated monomeric form of the Bax mutant cannot self associate as efficiently as the wild-type Bax (WT Bax), thereby resulting in a more relaxed structure. Based on its secondary structure assembly, the isolated purified Bax should be functional.

Figure 7B:
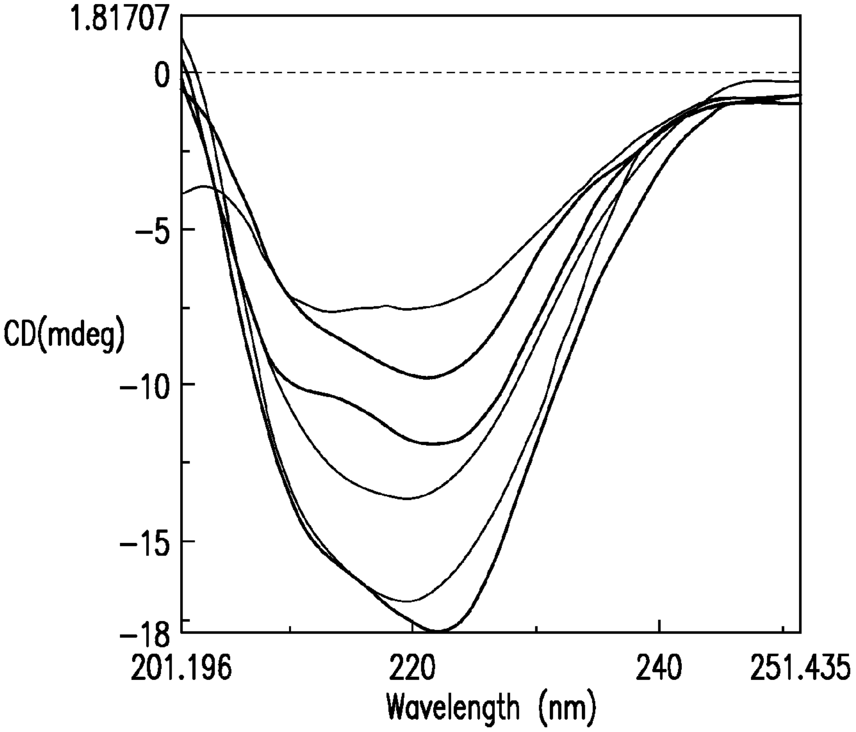
Figure 7C:
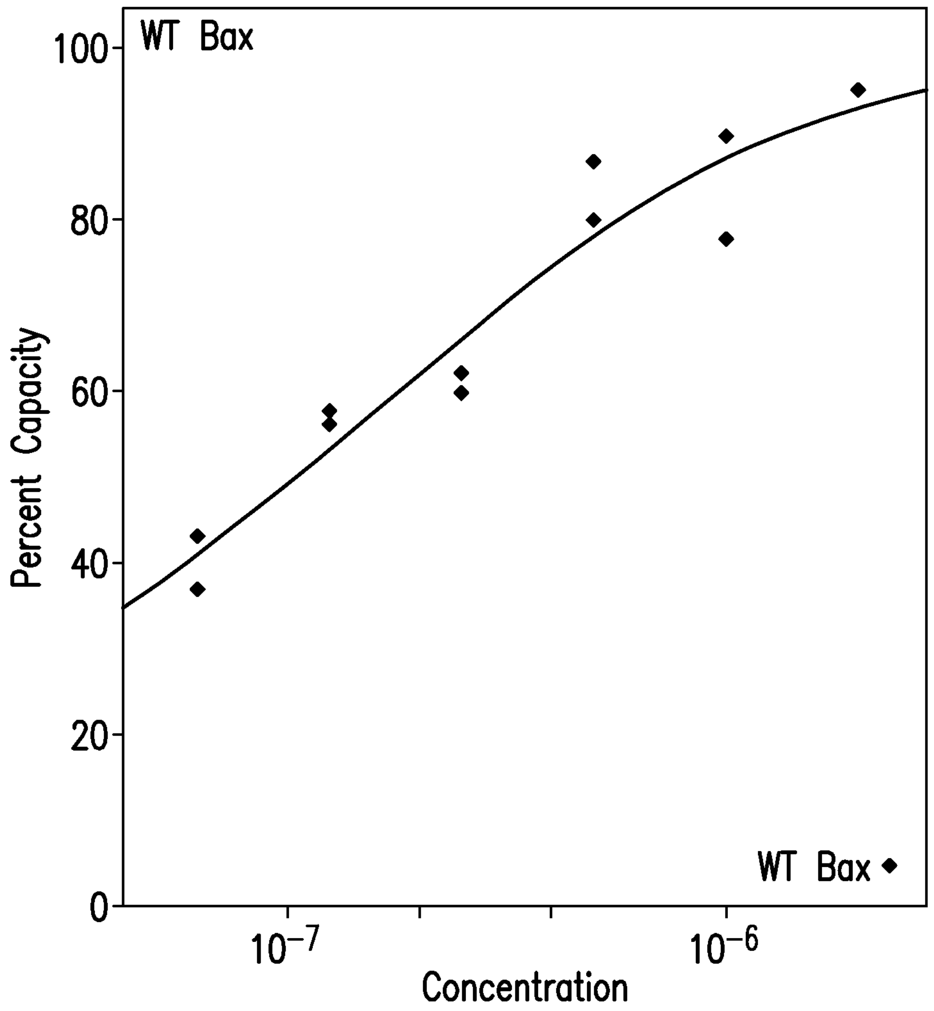

In FIG. 7B, the circular dichroism (CD) of the fractions from ion exchange chromatography showed the alpha-helical component of the purified protein. The minima at ~220 nm at all dilutions indicate a predominant alpha-helical component. These data indicate that after purification and based on its secondary structure assembly, the isolated Bax can be functional.

H. Sequences

SEQ ID NO:1, which represents the amino acid sequence for wild-type human Bax protein, is: MDGSGEQPRG GGPTSSEQIM KTGALLLQGF IQDRAGRMGG EAPELALDPV PQDASTKKLS ECLKRIGDEL DSNMELQRMI AAVDTDSPRE VFFRVAADMF SDGNFNWGRV VALFYFASKL VLKALCTKVP ELIRTIMGWT LDFLRERLLG WIQDQGGWDG LLSYFGTPTW QTVTIFVAGV LTASLTIWKK MG.

SEQ ID NO:2, which represents the amino acid sequence for the HMM peptide tag, is: MWWRLWWLLLLLLLLWP-MVWA.

SEQ ID NO:3, which represents the nucleotide sequence for wild-type Bax protein with HMM peptide tag, is: GAA TCC ATG TGG TGG CGC CTG TGG TGG CTG CTG CTG CTG CTG CTG CTG CTG TGG CCC ATG GTG TGG GCC GAC GGG TCC GGG GAG CAG CCC AGA GGC GGG GGG CCC ACC AGC TCT GAG CAG ATC ATG AAG ACA GGG GCC CTT TTG CTT CAG GGT TTC ATC CAG GAT CGA GCA GGG CGA ATG GGG GGG GAG GCA CCC GAG CTG GCC CTG GAC CCG GTG CCT CAG GAT GCG TCC ACC AAG AAG CTG AGC GAG TGT CTC AAG CGC ATC GGG GAC GAA CTG GAC AGT AAC ATG GAG CTG CAG AGG ATG ATT GCC GCC GTG GAC ACA GAC TCC CCC CGA GAG GTC TTT TTC CGA GTG GCA GCT GAC ATG TTT TCT GAC GGC AAC TTC AAC TGG GGC CGG GTT GTC GCC CTT TTC TAC TTT GCC AGC AAA CTG GTG CTC AAG GCC CTG TGC ACC AAG GTG CCG GAA CTG ATC AGA ACC ATC ATG GGC TGG ACA TTG GAC TTC CTC CGG GAG CGG CTG TTG GGC TGG ATC CAA GAC CAG GGT GGT TGG GAC GGC CTC CTC TCC TAC TTT GGG ACG CCC ACG TGG CAG ACC GTG ACC ATC TTT GTG GCG GGA GTG CTC ACC GCC TCA CTC ACC ATC TGG AAG AAG ATG GGC CTC GAG SEQ ID NO:4, which represents the nucleotide sequence for the HMM peptide tag, is: ATG TGG TGG CGC CTG TGG TGG CTG CTG CTG CTG CTG CTG CTG CTG TGG CCC ATG GTG TGG GCC.

SEQ ID NO:5, which represents the nucleotide sequence for wild-type Bax protein without the HMM peptide tag, is: ATG GAC GGG TCC GGG GAG CAG CCC AGA GGC GGG GGG CCC ACC AGC TCT GAG CAG ATC ATG AAG ACA GGG GCC CTT TTG CTT CAG GGT TTC ATC CAG GAT CGA GCA GGG CGA ATG GGG GGG GAG GCA CCC GAG CTG GCC CTG GAC CCG GTG CCT CAG GAT GCG TCC ACC AAG AAG CTG AGC GAG TGT CTC AAG CGC ATC GGG GAC GAA CTG GAC AGT AAC ATG GAG CTG CAG AGG ATG ATT GCC GCC GTG GAC ACA GAC TCC CCC CGA GAG GTC TTT TTC CGA GTG GCA GCT GAC ATG TTT TCT GAC GGC AAC TTC AAC TGG GGC CGG GTT GTC GCC CTT TTC TAC TTT GCC AGC AAA CTG GTG CTC AAG GCC CTG TGC ACC AAG GTG CCG GAA CTG ATC AGA ACC ATC ATG GGC TGG ACA TTG GAC TTC CTC CGG GAG CGG CTG TTG GGC TGG ATC CAA GAC CAG GGT GGT TGG GAC GGC CTC CTC TCC TAC TTT GGG ACG CCC ACG TGG CAG ACC GTG ACC ATC TTT GTG GCG GGA GTG CTC ACC GCC TCA CTC ACC ATC TGG AAG AAG ATG GGC CTC GAG.

SEQ ID NO:6, which represents the 20 amino acids at the C-terminal end of wild-type Bax protein, is: VTIFVAGVL-TASLTIWKKMG.

SEQ ID NO:7, which represents the 20 amino acids at the C-terminal end of wild-type Bax protein with two amino acid substitutions (i.e., EE for KK), is: VTIFVAGVLTASLTI-WEEMG.

SEQ ID NO:8, which represents the 20 amino acids at the C-terminal end of wild-type Bax protein with two amino acid substitutions (i.e., LL for KK), is: VTIFVAGVLTASLTI-WLLMG.

SEQ ID NO:9, which represents the 20 amino acids at the C-terminal end of wild-type Bax protein with two amino acid substitutions (i.e., RR for KK), is: VTIFVAGVLTASLTIWR-RMG.

I. REFERENCES

Antignani A, et al. 2006. How do Bax and Bak lead to permeabilization of the outer mitochondrial membrane? Curro Opin. Cell Biol. 18:685-689.

Antonsson B, et al. 2001. Bax is present as a high molecular weight oligomer/complex in the mitochondrial membrane of apoptotic cells. J. Biol. Chem. 276: 1161511623.

Boohaker R J, et al. 2011. BAX supports the mitochondrial network, promoting bioenergetics in nonapoptotic cells. Am J Physiol Cell Physiol; 300(6):C1466-C1478.

Brustovetsky T, et al. 2010. BAX insertion, oligomerization, and outer membrane permeabilization in brain mitochondria: role of permeability transition and SH-redox regulation. Biochim. Biophys. Acta. 1797: 1795-1806.

Cartron P F, et al. 2005. Distinct domains control the addressing and the insertion of Bax into mitochondria. J Biol Chern; 280(11): 10587-98.

Cartron P F, et al. 2004. The first alpha helix of Bax plays a necessary role in its ligand-induced activation by the BH3-only proteins Bid and PUMA. Mol Cell; 16(5):807-18.

Eskes R, et al. 1998. Bax induced cytochrome C release from mitochondria is independent of the permeability transition pore but highly dependent on Mg2+ ions. J Cell Biol; 143(1):21724.

Garcia-Saez A J, et al. 2010. Permeabilization of the outer mitochondrial membrane by Bcl-2 proteins. Adv. Exp. Med. Biol. 677:91-105.

Gavathiotis E, et al. 2008. BAX activation is initiated at a novel interaction site. Nature; 455(7216): 1076-81.

Ghibelli L, et al. 2010. Multistep and multitask Bax activation. Mitochondrion. 10:604-613.

Kaufmann T, et al. 2003. Characterization of the signal that directs Bcl-x(L), but not Bcl-2, to the mitochondrial outer membrane. J Cell Biol; 160(1):53-64.

Kelekar A, et al. 1998. Bcl-2-family proteins: the role of the BH3 domain in apoptosis. Trends Cell Biol; 8(8):324-30.

Leber B, et al. 2007. Embedded together: The life and death consequences of interaction of the Bcl-2 family with membranes. Apoptosis. 12:897-911.

Oltvai Z N, et al. Bcl-2 heterodimerizes in vivo with a conserved homolog, Bax, that accelerates programmed cell death. Cell 1993 Aug. 27; 74(4):609-19.

Putcha G V, et al. BAX translocation is a critical event in neuronal apoptosis: regulation by neuroprotectants, BCL-2, and caspases. J Neurosci 1999 Sep. 1; 19(17):7476-85.

Robertson J D, et al. 2003. Outer mitochondrial membrane permeabilization: an open-and-shut case? Cell Death Differ. 10:485-487.

Roucou X, et al. 2002. Bax oligomerization in mitochondrial membranes requires tBid (caspase-8-cleaved Bid) and a mitochondrial protein. Biochem. J. 368:915-921.

Suzuki M, et al. Structure of Bax: coregulation of dimer formation and intracellular localization. Cell 2000 Nov. 10; 103(4):645-54.

Tait S W, et al. 2010. Mitochondria and cell death: outer membrane permeabilization and beyond. Nat. Rev. Mol. Cell. Biol. 11:621-632.

Valero G, et al. 2011. Bax-derived membrane-active peptides act as potent and direct inducers of apoptosis in cancer cells. J. Cell Sci. 124:556-564.

Westphal D, et al. Molecular biology of Bax and Bax activation and action. Biochim Biophys Acta 2011 April; 1813(4):521-31.

Westphal D, et al. 2011. Molecular biology of Bax and Bak activation and action. Biochim. Biophys. Acta. 1813:521-531.

Youle R J, et al. 2008. The BCL-2 protein family: opposing activities that mediate cell death. Nat. Rev. Mol. Cell. Bio!. 9:47-59.

Zhou L, et al. 2008. Dynamics and structure of the Bax-Bak complex responsible for releasing mitochondrial proteins during apoptosis. J. Cell Sci. 121:2186-2196.

The invention claimed is:

1. A method of purifying a Bax protein, comprising: modifying a nucleic acid encoding a Bax protein to further encode an HMM peptide; expressing the modified nucleic acid in a host cell; and culturing the host cell in a medium; harvesting the medium; and purifying the Bax protein from the harvested medium, wherein the HMM peptide has 99%, 98%, 97%, 96%, 95%, 94%, 93% 92%, 91%, or 90% sequence identity to MWWRLWWLLLLLLLLWPMVWA (SEQ ID NO:2).

2. The method of claim 1, further comprising concentrating the harvested medium.

3. The method of claim 1, further comprising assessing Bax protein content, Bax protein concentration, Bax protein conformation integrity, or Bax protein activity.

4. The method of claim 1, wherein the host cell is a mammalian cell.

5. The method of claim 1, wherein the HMM peptide is MWWRLWWLLLLLLLLWPMVWA (SEQ ID NO:2).

6. The method of claim 1, wherein the Bax protein is encoded by a nucleotide sequence of SEQ ID NO:5.

7. The method of claim 1, wherein the modified nucleic acid comprises the nucleotide sequence of SEQ ID NO:3.

8. The method of claim 1, wherein the purified Bax protein is wild-type Bax.

9. The method of claim 1, wherein the purified Bax protein is a mutant Bax protein.

10. The method of claim 9, wherein the purified mutant Bax protein comprises a C-terminal deletion.

* * * * *

SEQUENCE LISTING

```
<160> NUMBER OF SEQ ID NOS: 9

<210> SEQ ID NO 1
<211> LENGTH: 192
<212> TYPE: PRT
<213> ORGANISM: Artificial Sequence
<220> FEATURE:
<223> OTHER INFORMATION: Synthetic Construct

<400> SEQUENCE: 1

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80
```

-continued

```
Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190
```

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

```
Met Trp Trp Arg Leu Trp Trp Leu Leu Leu Leu Leu Leu Leu Leu Trp
1               5                   10                  15

Pro Met Val Trp Ala
            20
```

<210> SEQ ID NO 3
<211> LENGTH: 648
<212> TYPE: DNA
<213> ORGANISM: Artificial Sequence
<220> FEATURE:
<223> OTHER INFORMATION: Synthetic Construct

<400> SEQUENCE: 3

```
gaatccatgt ggtggcgcct gtggtggctg ctgctgctgc tgctgctgct gtggcccatg      60

gtgtgggccg acgggtccgg ggagcagccc agaggcgggg ggcccaccag ctctgagcag     120

atcatgaaga caggggccct tttgcttcag ggtttcatcc aggatcgagc agggcgaatg     180

ggggggggagg cacccgagct ggccctggac ccggtgcctc aggatgcgtc caccaagaag    240

ctgagcgagt gtctcaagcg catcggggac gaactggaca gtaacatgga gctgcagagg     300

atgattgccg ccgtggacac agactccccc cgagaggtct ttttccgagt ggcagctgac     360

atgttttctg acggcaactt caactggggc cgggttgtcg cccttttcta ctttgccagc     420

aaactggtgc tcaaggccct gtgcaccaag gtgccggaac tgatcagaac catcatgggc     480

tggacattgg acttcctccg ggagcggctg ttgggctgga tccaagacca gggtggttgg     540

gacggcctcc tctcctactt tgggacgccc acgtggcaga ccgtgaccat ctttgtggcg     600

ggagtgctca ccgcctcact caccatctgg aagaagatgg gcctcgag                  648
```

<210> SEQ ID NO 4
<211> LENGTH: 63
<212> TYPE: DNA
<213> ORGANISM: Artificial Sequence
<220> FEATURE:
<223> OTHER INFORMATION: Synthetic Construct

<400> SEQUENCE: 4

-continued atgtggtggc gcctgtggtg gctgctgctg ctgctgctgc tgctgtggcc catggtgtgg 60
gcc 63

<210> SEQ ID NO 5
<211> LENGTH: 576
<212> TYPE: DNA
<213> ORGANISM: Artificial Sequence
<220> FEATURE:
<223> OTHER INFORMATION: Synthetic Construct

<400> SEQUENCE: 5
atggacgggt ccggggagca gcccagaggc ggggggccca ccagctctga gcagatcatg 60
aagacagggg cccttttgct tcagggtttc atccaggatc gagcagggcg aatggggggg 120
gaggcacccg agctggccct ggacccggtg cctcaggatg cgtccaccaa gaagctgagc 180
gagtgtctca agcgcatcgg ggacgaactg gacagtaaca tggagctgca gaggatgatt 240
gccgccgtgg acacagactc cccccgagag gtctttttcc gagtggcagc tgacatgttt 300
tctgacggca acttcaactg gggccgggtt gtcgcccttt tctactttgc cagcaaactg 360
gtgctcaagg ccctgtgcac caaggtgccg gaactgatca gaaccatcat gggctggaca 420
ttggacttcc tccgggagcg gctgttgggc tggatccaag accagggtgg ttgggacggc 480
ctcctctcct actttgggac gcccacgtgg cagaccgtga ccatctttgt ggcgggagtg 540
ctcaccgcct cactcaccat ctggaagaag atgggc 576

<210> SEQ ID NO 6
<211> LENGTH: 20
<212> TYPE: PRT
<213> ORGANISM: Artificial Sequence
<220> FEATURE:
<223> OTHER INFORMATION: Synthetic Construct

<400> SEQUENCE: 6

Val Thr Ile Phe Val Ala Gly Val Leu Thr Ala Ser Leu Thr Ile Trp
1 5 10 15

Lys Lys Met Gly
20

<210> SEQ ID NO 7
<211> LENGTH: 20
<212> TYPE: PRT
<213> ORGANISM: Artificial Sequence
<220> FEATURE:
<223> OTHER INFORMATION: Synthetic Construct

<400> SEQUENCE: 7

Val Thr Ile Phe Val Ala Gly Val Leu Thr Ala Ser Leu Thr Ile Trp
1 5 10 15

Glu Glu Met Gly
20

<210> SEQ ID NO 8
<211> LENGTH: 20
<212> TYPE: PRT
<213> ORGANISM: Artificial Sequence
<220> FEATURE:
<223> OTHER INFORMATION: Synthetic Construct

<400> SEQUENCE: 8

Val Thr Ile Phe Val Ala Gly Val Leu Thr Ala Ser Leu Thr Ile Trp
1 5 10 15

-continued

```
Leu Leu Met Gly
            20


<210> SEQ ID NO 9
<211> LENGTH: 20
<212> TYPE: PRT
<213> ORGANISM: Artificial Sequence
<220> FEATURE:
<223> OTHER INFORMATION: Synthetic Construct

<400> SEQUENCE: 9

Val Thr Ile Phe Val Ala Gly Val Leu Thr Ala Ser Leu Thr Ile Trp
1               5                   10                  15

Arg Arg Met Gly
            20
```